(12) United States Patent
Kuehn

(10) Patent No.: US 12,337,151 B2
(45) Date of Patent: Jun. 24, 2025

(54) STOPPER

(71) Applicant: SANOFI, Paris (FR)

(72) Inventor: Bernd Kuehn, Frankfurt am Main (DE)

(73) Assignee: Sanofi, Paris (FR)

( * ) Notice: Subject to any disclaimer, the term of this patent is extended or adjusted under 35 U.S.C. 154(b) by 918 days.

(21) Appl. No.: 16/968,735

(22) PCT Filed: Feb. 8, 2019

(86) PCT No.: PCT/EP2019/053195
§ 371 (c)(1),
(2) Date: Aug. 10, 2020

(87) PCT Pub. No.: WO2019/155018
PCT Pub. Date: Aug. 15, 2019

(65) Prior Publication Data
US 2021/0001053 A1   Jan. 7, 2021

(30) Foreign Application Priority Data
Feb. 12, 2018  (EP) .................................... 18305141

(51) Int. Cl.
*A61M 5/315*  (2006.01)
*A61M 5/20*  (2006.01)
(Continued)

(52) U.S. Cl.
CPC ...... *A61M 5/31563* (2013.01); *A61M 5/2455* (2013.01); *A61M 5/31513* (2013.01);
(Continued)

(58) Field of Classification Search
CPC ............ A61M 5/31563; A61M 5/2455; A61M 5/31513; A61M 5/20; A61M 2005/2492;
(Continued)

(56) References Cited

U.S. PATENT DOCUMENTS 4,180,069 A * 12/1979 Walters ............. A61M 5/31515
604/228
4,500,310 A    2/1985 Christinger
(Continued)

FOREIGN PATENT DOCUMENTS

EP           0111724       6/1984
JP         S59-115053      7/1984
(Continued)

OTHER PUBLICATIONS

Definition of convex (Year: 2024).*
(Continued)

*Primary Examiner* — Dung T Ulsh
(74) *Attorney, Agent, or Firm* — Fish & Richardson P.C.

(57) ABSTRACT

A stopper for use in a cartridge or syringe of a medical device $_{[SL6]}$ is configured to be disposed within a container closure system. The stopper comprises a shell comprising a closed end and an open end with sidewalls extending between the closed end and the open end along a longitudinal axis of the shell. The open end defines a cavity and the sidewalls define an exterior surface sized and shaped to fit inside the container closure system. An insert is configured to be inserted into the cavity, receive a force from a plunger rod, and distribute the force to the shell in order to advance the shell into the container closure system. The closed end of the shell in the cavity defining a convex surface configured to be contacted and deflected by the insert upon insertion into the cavity includes an elastic and/or plastic deformable material.

19 Claims, 23 Drawing Sheets

(51) Int. Cl.
  *A61M 5/24* (2006.01)
  *A61M 5/31* (2006.01)
(52) U.S. Cl.
  CPC ....... *A61M 5/20* (2013.01); *A61M 2005/2492* (2013.01); *A61M 2005/3123* (2013.01); *A61M 2205/3327* (2013.01)
(58) Field of Classification Search
  CPC .. A61M 2005/3123; A61M 2205/3327; A61M 5/31511; A61M 5/31515; A61M 5/315
  See application file for complete search history.

(56) References Cited

U.S. PATENT DOCUMENTS

| | | | | |
|---|---|---|---|---|
| 4,543,093 | A * | 9/1985 | Christinger | A61M 5/31513 604/228 |
| 5,865,798 | A | 2/1999 | Grimard et al. | |
| 2003/0120220 | A1 | 6/2003 | Lee et al. | |
| 2007/0219507 | A1 | 9/2007 | Dai et al. | |
| 2014/0249410 | A1 * | 9/2014 | Uber, III | A61M 5/20 604/246 |
| 2016/0151570 | A1 | 6/2016 | Rhinehart et al. | |
| 2017/0216528 | A1 | 8/2017 | Pommereau et al. | |
| 2017/0281853 | A1 | 10/2017 | Luo et al. | |
| 2017/0312430 | A1 | 11/2017 | Schleicher et al. | |
| 2017/0312455 | A1 | 11/2017 | Mirov et al. | |
| 2018/0147361 | A1 * | 5/2018 | Holland | A61M 5/00 |
| 2019/0125976 | A1 * | 5/2019 | Lilly | A61F 9/0008 |
| 2020/0086057 | A1 * | 3/2020 | Swantner | A61M 5/31513 |
| 2020/0316304 | A1 * | 10/2020 | Törnsten | A61M 5/3202 |

FOREIGN PATENT DOCUMENTS

| | | |
|---|---|---|
| JP | 2007-517613 | 7/2007 |
| JP | 2010-528773 | 8/2010 |
| JP | 2012-029918 A | 2/2012 |
| WO | WO 2005/070485 | 8/2005 |
| WO | WO 2008/151239 | 12/2008 |
| WO | WO 2011/121867 A1 | 10/2011 |
| WO | WO 2017/011599 | 1/2017 |
| WO | WO 2017/084057 | 5/2017 |

OTHER PUBLICATIONS

PCT International Preliminary Report on Patentability in International Appln. No. PCT/EP2019/053195, dated Aug. 18, 2020, 7 pages.
PCT International Search Report and Written Opinion in International Appln. No. PCT/EP2019/053195, dated Mar. 14, 2019, 9 pages.

* cited by examiner

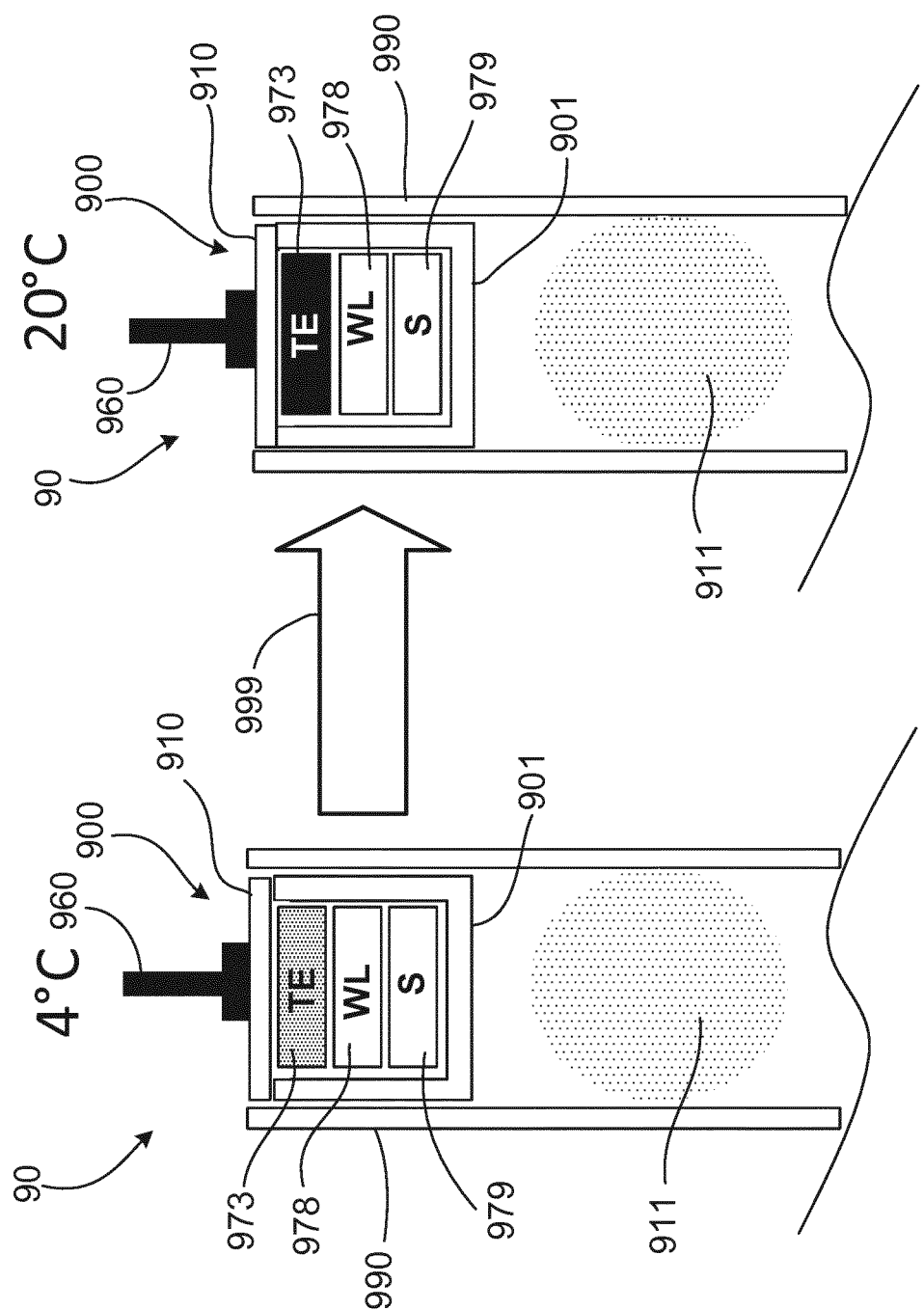

STOPPER

CROSS REFERENCE TO RELATED APPLICATIONS

The present application is the national stage entry of International Patent Application No. PCT/EP2019/053195, filed on Feb. 8, 2019, and claims priority to Application No. EP 18305141.6, filed on Feb. 12, 2018, the disclosures of which are incorporated herein by reference.

TECHNICAL FIELD

This description relates to a stopper for use in a cartridge or syringe of a medical device configured to eject a medicament using the stopper.

BACKGROUND

A variety of diseases exist that require treatment by injection of a medicament. Such injection can be performed using injection devices, which are applied either by medical personnel or by patients themselves. As an example, type-1 and type-2 diabetes can be treated by patients themselves by injection of insulin doses, for example once or several times per day. For instance, a pre-filled disposable insulin pen or autoinjector can be used as an injection device. Alternatively, a re-usable pen or autoinjector may be used. A re-usable pen or autoinjector allows replacement of an empty medicament cartridge by a new one. Each of these devices typically employs an elastomeric stopper or bung to drive a medicament from the cartridge or a syringe in the device and some include one or more electronic devices embedded in the stopper.

SUMMARY

An example disclosure of the present embodiment is a stopper for use in a cartridge or syringe of a medical device, the stopper configured to be disposed within a container closure system, the stopper comprising a shell comprising a closed end and an open end with sidewalls extending between the closed end and the open end along a longitudinal axis of the shell, the open end defining a cavity and the sidewalls defining an exterior surface sized and shaped to fit inside the container closure system; and an insert configured to be inserted into the cavity, the insert sized and shaped to receive a force from a plunger rod and distribute the force to the shell in order to advance the shell into the container closure system, wherein the a closed end of the shell in the cavity defines a convex surface configured to be contacted and deflected by the insert upon insertion into the cavity, and wherein the closed end of the shell is made of an elastic and/or plastic deformable material.

The closed end of the shell may define an arch region defining the convex surface in the cavity and a concave surface of the exterior of the closed end of the shell, and the arch region may be configured to be deflected by the insert contacting the convex surface during insertion into the cavity.

The cavity may define inwardly tapering sidewalls from the open end to the closed end of the shell, and the inwardly tapering sidewalls may be configured to maintain an inward taper when the arch region is deflected by the insert.

The cavity may comprise an interior step element, and the insert may comprise a corresponding step element configured to abut the interior step element of the shell and distribute at least a portion of the force from the plunger rod to the interior step element.

The cavity may define a snap-fit feature extending into the cavity, the snap-fit feature configured to retain the insert in the cavity by being deflected or deformed by the insert during insertion of the insert into the cavity until the snap-fit feature relaxes into a corresponding depression in the insert, and an exterior surface of the insert may define the corresponding depression being sized and positioned to accept the snap-fit feature.

The corresponding step element may be sized and positioned to retain the interior step element and resist radial deflection of the interior step element by the force applied to the insert.

The interior step element may define a first interface surface, and the corresponding step element may define a second interface surface, and insertion of the insert into the shell may abut the first interface surface against the second interface surface.

The first interface surface and the second interface surface may define acute angles about the closed end of the shell.

The cavity may comprise at least one venting channel extending from the closed end of the shell towards the open end of the shell, the at least one venting channel being sized and positioned to enable air and/or fluid in the cavity to be expelled though the at least one venting channel during insertion of the insert into the cavity.

The at least one venting channel may extend partially towards the open end of the shell and not extend fully to the open end of the shell.

The insert may define a conically tapering exterior surface configured to enable venting of air in the cavity around the exterior of the insert during insertion of the insert.

The insert may comprise an electronic device having a sensor configured to generate a sensing signal, and the closed end of the shell may be configured to pass the sensing signal therethrough.

The sensor may be configured to be responsive to position of the stopper in the container closure system.

Another example embodiment of the present disclosure is a container closure system comprising a cartridge or syringe housing and a stopper as described above, wherein the shell is configured to be inserted into the housing prior to the container closure system being filled with the medical product, and the insert is configured to be inserted into the stopper after the filling procedure.

The container closure system may comprise a syringe, and the cartridge housing may be a housing of the syringe, and the insert may be disposed at a distal end of plunger rod of the syringe configured to be inserted into the shell of the stopper after the syringe is assembled into a medical device.

The housing may be configured for use with one or more of: an autoinjector, a pen injector, and an injection pump.

The cartridge or syringe housing may contain a liquid medicament.

Another example embodiment of the present disclosure is a stopper configured to be disposed within a container closure system. The stopper includes a shell and an insert configured to be inserted into a cavity of the shell. The shell includes a closed end and an open end with sidewalls extending between the closed end and the open end along a longitudinal axis of the shell, the open end defining a cavity and the sidewalls defining an exterior surface sized and shaped to fit inside the container closure system, with the cavity having an interior step element. The insert is sized and shaped to receive a force from a plunger rod and distribute the force to the shell in order to advance the shell into the container closure system. The insert includes a corresponding step element configured to abut the interior step element of the shell and distribute at least a portion of the force from the plunger rod to the interior step element.

In some examples, the cavity defines a snap-fit feature extending into the cavity, the snap-fit feature configured to retain the insert in the cavity by being deflected or deformed by the insert during insertion of the insert into the cavity until the snap-fit feature relaxes into a corresponding depression in the insert, and wherein an exterior surface of the insert defines the corresponding depression being sized and positioned to accept the snap-fit feature.

In some examples, the snap-fit feature extends radially around the cavity.

In some examples, the corresponding depression extends radially around the exterior surface of the insert.

In some examples, the corresponding step element is sized and positioned to retain the interior step element and resist radial deflection of the interior step element by the force applied to the insert.

In some examples, the interior step element defines a first interface surface, and wherein the corresponding step element defines a second interface surface, and wherein insertion of the insert into the shell abuts the first interface surface against the second interface surface. In some examples, the first and second interface surfaces define an acute angle about the closed end of the shell.

In some examples, the insert is sized and shaped to fit completely within the cavity when inserted.

In some examples, the insert, when inserted, defines a contact surface above the open end of the shell with respect to the longitudinal axis.

In some examples, the cavity defines a venting channel extending from the open end of the cavity to a rearward end of the cavity opposite the open end, the venting channel being sized and positioned to enable air and/or fluid in the cavity to be expelled though the venting channel during insertion of the insert into the cavity. In some examples, the venting channel extends radially along at least a length of the rearward end of the cavity.

In some examples, the insert defines a conically tapering exterior surface configured to enable venting of air in the cavity around the exterior of the insert during insertion of the insert.

In some examples, the insert includes an electronic device having a sensor configured to generate a sensing signal, wherein the closed end of the shell is configured to pass the sensing signal therethrough.

In some examples, the sensor is configured to be responsive to position of the stopper in the container closure system.

In some examples, in the insert includes a cap member configured to seal the open end of the cavity against the insert when the insert is inserted into the cavity.

In some examples, the insert is configured to be secured to the shell using one or more of the following: a snap-fit feature, glue, welding, ultrasonic welding, friction welding, or thermal welding.

In some examples, the shell is constructed from a material that can be sterilized.

In some examples, the insert is a distal end of the plunger rod.

In some examples, the stopper includes a sealing member disposed around an exterior surface of the sidewalls and arranged to form a seal between the exterior surface and an inner surface of the container closure system when the stopper is disposed within the container closure system.

In some examples, the shell is a soft shell including a substantially pliable material.

In some examples, an exterior surface of the sidewalls of the soft shell defines a sealing region radially around the exterior surface and arranged to form a seal between the exterior surface and an inner surface of the container closure system when the stopper is disposed within the container closure system.

In some examples, wherein the closed end of the shell defines a convex shape in the cavity configured to be contacted and deflected by the insert upon insertion into the cavity.

In some examples, the closed end of the shell defines an arch region defining the convex shape in the cavity and a concave surface of the exterior of the closed end of the shell, and wherein the arch region is configured to be deflected by the insert upon insertion into the cavity.

Another example is a container closure system including a cartridge or syringe housing and a stopper configured to be disposed within the container closure system. The stopper includes a shell and an insert configured to be inserted into a cavity of the shell. The shell includes a closed end and an open end with sidewalls extending between the closed end and the open end along a longitudinal axis of the shell, the open end defining a cavity and the sidewalls defining an exterior surface sized and shaped to fit inside the container closure system, with the cavity having an interior step element. The insert is sized and shaped to receive a force from a plunger rod and distribute the force to the shell in order to advance the shell into the container closure system. The insert includes a corresponding step element configured to abut the interior step element of the shell and distribute at least a portion of the force from the plunger rod to the interior step element. The shell is configured to be inserted into the cartridge or syringe prior to the container closure system is being filled with the medical product, and the insert is configured to be inserted into the stopper after the filling procedure.

In some examples, the medical cartridge is a syringe, and the cartridge housing is a housing of the syringe, and wherein the insert is a disposed at the distal end of the plunger rod of the syringe configured to be inserted into the shell of the stopper after the syringe is assembled into a medical device.

In some examples, the housing is configured for use with an autoinjector.

In some examples, the housing is configured for use with a pen injector

In some examples, the housing is configured for use with an injection pump.

In some instances, the medicament includes a pharmaceutically active compound.

Another example is a stopper configured to be disposed within a container closure system. The stopper includes a shell having a closed end and an open end with sidewalls extending between the closed end and the open end along a longitudinal axis of the shell and an insert configured to be inserted into a cavity of the stopper, the insert being sized and shaped to receive a force from a plunger rod and distribute the force to the shell in order to advance the shell into the container closure system. The open end of the stopper defines the cavity and the sidewalls define an exterior surface sized and shaped to fit inside the container closure system. The closed end of the shell defines an arch region defining a convex surface at a closed end of the cavity and a concave surface of the exterior of the closed end of the shell, and wherein the arch region is configured to be deflected by the insert contacting the convex region upon insertion into the cavity.

In some instances, the cavity defines inwardly tapering sidewalls from the open end to the closed end of the cavity, and wherein the inwardly tapering sidewalls are configured to maintain an inward taper when the arch region is deflected by the insert.

Yet another example is a stopper configured to be disposed within a container closure system, where the stopper includes a shell having a closed end and an open end with sidewalls extending between the closed end and the open end along a longitudinal axis of the shell, where the open end defines a cavity and the sidewalls define an exterior surface sized and shaped to fit inside an inner surface of the container closure system. The stopper includes a sealing element arranged around the exterior surface of the side walls, an insert configured to be inserted into the cavity, and a closure cap configured to be inserted into the cavity behind the insert and seal the insert inside the cavity, where the sealing element is configured to create a seal between the shell and the inner surface of the container closure system.

In some instances, the stopper includes an adhesive element configured to be disposed in the cavity at a closed end of the cavity and to adhere the insert to the shell, the adhesive element configured to receive a distal end of the insert during insertion of the insert into the cavity or during insertion of the closure cap into the cavity against a proximal end of the insert.

In some instances, the stopper includes a deformable element configured to be disposed in the cavity between the insert and the closure cap, where the deformable element is configured to be deformed by a distal end of the closure cap during insertion of the closure cap into the cavity.

In some instances, the stopper includes a deformable element configured to be disposed in the cavity at a closed end of the cavity, where the deformable element is configured to be deformed by a distal end of the insert during insertion of the insert into the cavity or during insertion of the closure cap into the cavity against a proximal end of the insert.

In general, the examples described herein relate to pharmaceutical closure components with a sensor insert for positioning an embedded electronics assembly into an operative location inside a cartridge or syringe cylinder.

BREIF DESCRIPTION OF THE FIGURES

FIGS. 9A and 9B are cross-sectional views of a stopper disposed within a cartridge and powered by a thermoelectric system.

DETAILED DESCRIPTION

Figure 1:
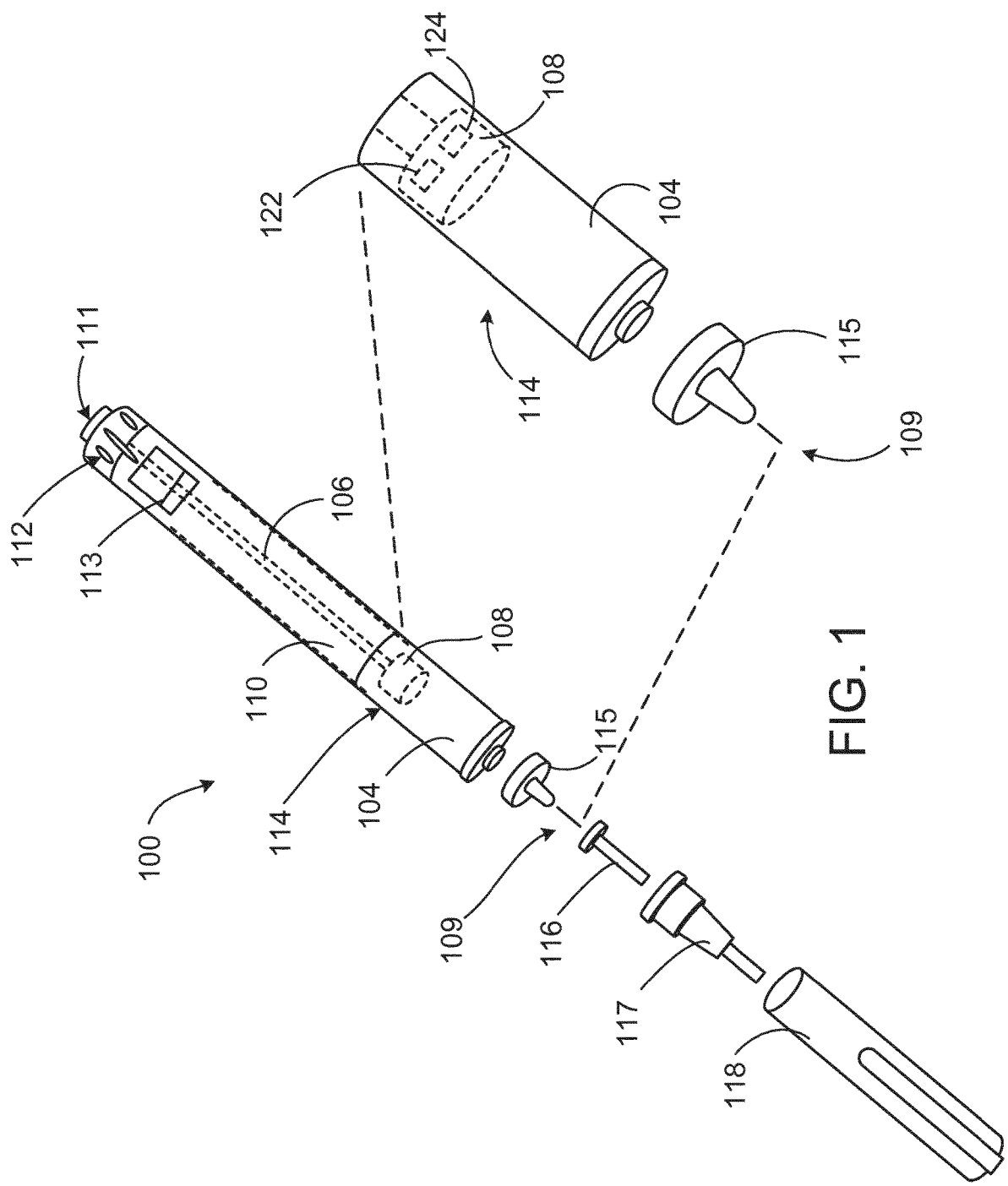
FIG. 1 is an exploded view of an injection device.

Information on the use of medical devices by patients can be determined by sensors that generate data, which can then be accessed through wireless communication. For injection devices, one or more sensors may be integrated into the stopper of a drug containing cartridge or syringe (also referred to as a plunger or plunger stopper). Wireless communication of the data requires an energy source, e.g., a battery cell, that also needs to be connected to the sensor and thus may be integrated into the stopper. Typical manufacturing processes for sterile plunger stoppers to be used in injection devices include process steps with high temperatures (e.g., rubber molding and steam sterilization processes), which may not be compatible with some electronic components (e.g., batteries). Therefore, some cartridge-based injection and medical syringe systems can be difficult to sterilize prior to use if they include electronics in the replaceable portions of the device (e.g., a cartridge stopper or a cartridge housing). In some instances, elements containing electronic assemblies may be separated from the plunger stopper to be assembled at a later stage after the sterilization processes are completed.

Electronic devices and assemblies may contain temperature sensitive materials (e.g., polymers) which may get degrade after heat is applied. Further, batteries can lose performance at high temperatures. To avoid exposure of the electronics components to excess heat, in some examples, part of the cartridge stopper (sometimes referred to as a bung) can be sterilized before the electronics are added. For example, a stopper shell can be forming a seal against a cartridge wall, and an insert containing electronic devices separate from the stopper can be used so that the insert is assembled into the stopper after a heat sterilization step (and, therefore, also without impacting the sterilized liquid inside the cartridge). In some instances, the insert is integrated into the distal end of a plunger rod of an injection device and is inserted into a stopper shell prior to use of the injection device. In some examples, electronic components (e.g., RFID sensors) can be added to a previously heat-sterilized stopper of a disposable or reusable drug cartridge.

Stoppers used in a drug containing cartridge or syringe typically fulfill functional requirements such as achieving dosing precision, maintaining container closure integrity, and providing certain force profiles with a feedback to the patient. Container closure systems, generally, include a cartridge or a syringe composed of a barrel, typically made of glass or plastic and a stopper plus a closure cap. As described in detail below, a shell of the stopper may define a cavity on the open or proximal end (the end opposite the drug-contacting end) configured to accept a sensor insert (also referred to simply as an insert) that, in some instances, contains functional electronic devices. In some instances, the insert being disposed in the cavity places an electronic device in close proximity to the volume enclosed by the stopper and thereby enables a sensor in the insert to conduct sensing operations of the volume (e.g., determining the location of the stopper in the cartridge). Assembling a sensor insert into a stopper may lead to the following issues that influence the functional requirements:

(i) Elastic deformation of the stopper under the impact of an injection force may affect dosing precision,
(ii) Movement of the sensor insert from its resting position in the stopper may affect dosing precision,
(iii) Misalignment of the sensor insert may tilt the stopper and affect container closure integrity,
(iv) Misalignment of the sensor insert may tilt the stopper and affect force profiles during an injection,
(v) Misalignment of the sensor insert may affect an ultrasonic sound emission and reception from a sensing unit in the insert, and thus jeopardize precise position measurement of the stopper in a cartridge or syringe,
(vi) Air inclusions between the sensor insert and the stopper may induce oscillation during a dosing operation and subsequently affect dosing precision, and
(vii) Air inclusion in front of a sensor insert may affect functionality of e.g. ultrasound measurement principles and thus leading to wrong results.

Accordingly, techniques described herein include stoppers having a shell with a cavity configured to accept a sensor insert to achieve appropriate injection force transmission, acceptable alignment and fixation of components, and avoid air inclusion, among other things. In operation, an injection force applied by a plunger rod presses onto the back end of a stopper and pushes the stopper forward in a cartridge, thus expelling a medicament from the cartridge. The cavity is formed in the back end of the stopper shell and a sensor insert is disposed in the cavity. With an insert in the shell, the plunger rod transmits the force to the sensor insert and, in some instances, the insert has a stepped shape that defines interface surfaces between each step, such that the force of the plunger on the insert is distributed to the stopper in a staggered manner through the interface surfaces against corresponding surfaces in the cavity of the stopper. In some embodiments, the stepped profile of the insert includes features configured to interface with the cavity and radially retain the cavity against the insert. In some instances, these features are configured to strengthen the radial fixation of the elastomer stopper to the insert during the transmission of the force from the insert to the stopper, and, as a result, reduce radial deflection of the cavity (i.e., away from the insert).

In some instances, once the sensor insert is assembled in its determined position in the stopper, it is fixed in-place with snap-fit elements. Such snap-fit elements may be circumferential rings of rubber material that match with corresponding grooves in the sensor insert element. One snap-fit element at the back end of the stopper and optionally further snap-fit elements can be applied.

In some instances, a sensor insert includes a circular shape with a smaller diameter at a distal section that is oriented towards the distal end of the stopper (i.e., the drug-contacting end), and a larger diameter of the proximal section that is at the proximal end of the stopper. In some instances, the distal section of the sensor insert contains a sensor element and the proximal section contains a power source (e.g., a battery cell) connected to the sensor element. Additional electronic components (e.g. an integrated circuit or a printed circuit board) may be placed in between (or integrated with) the sensor element and the power source, or in a different configuration, which is, in some instances, determined by the preferred location of the sensor element in the stopper in order to conduct a sensing operation. In some instances, the cavity inside the stopper narrows down from the distal to the proximal end and provides guidance for the insertion of the sensor insert. In one embodiment, the sensor insert is cone-shaped with a matching design of the stopper inner cavity to allow insertion of the sensor insert without friction between rubber material of the stopper and the sensor insert until the snap-fit features engage to retain the sensor insert in place in the cavity. In an alternate embodiment, threads may be used in addition to snap-fit features to lock the sensor insert into position.

In addition to the cone-shape design of the interface, in some instances, one or more lateral channels to allow air to vent before becoming trapped in dead ends are provided. In addition, a front end of the cavity may have a convex shape extending into the cavity to allow the insert to make a first central contact with the rubber shell to expel entrapped air from the dead end. In some instances, the closed end of the stopper defines an arch shape that includes the convex shape of the end of the cavity a concave exterior surface of the distal end of the shell. In some instances, the closed end of the cavity includes extending lateral channels configured to vent the air from the cavity when the insert is inserted.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N- myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

FIG. 1 is an exploded view of an injection device 100, which may be a disposable or reusable injection device. The injection device 100 includes a housing 110 and a having therein a cartridge 114 with cartridge housing 104, to which a needle assembly 115 can be affixed. The needle 109 of needle assembly 115 is protected by an inner needle cap 116 and an outer needle cap 117, which in turn can be covered by cap 118. A medicament or drug dose to be ejected from the injection device 100 is selected by turning a dosage knob 112, and the selected dose is displayed via a dosage window or display 113. The display can include a digital display, for example. The dosage display 113 relates to the section of the injection device through or on which the selected dosage is visible.

As described further below, the injection device 100 may include one or more electronic components 122, 124, some of which may be included in the stopper 108, for example.

Turning the dosage knob 112 causes a mechanical click sound to provide acoustical feedback to a user. The numbers displayed in the dosage display 113 are printed on a sleeve that is contained in the housing 110 and mechanically interacts with a stopper in the cartridge 114. When the needle 109 is stuck into a skin portion of a patient, and then the injection button 111 is pushed, the drug dose displayed in the display 113 will be ejected from the injection device 100. During an injection, a drive mechanism 106, which is shown as an outline of a plunger arm, drives a stopper 108 into the cartridge to expel the drug. The stopper is an important element of the container closure system because it is a barrier for fluids leaking in and out; a gas barrier (e.g., oxygen), and prevents evaporation of H2O and other fluids. In some embodiments, the seal function is provided by sealing elements (604, 605 of FIG. 6A) in contact with the container walls, but still allows the stopper to glide. When the needle 109 of injection device 100 remains for a certain time in the skin portion after the injection button 111 is pushed, a high percentage of the dose is actually injected into the patient's body.

Figure 2A:
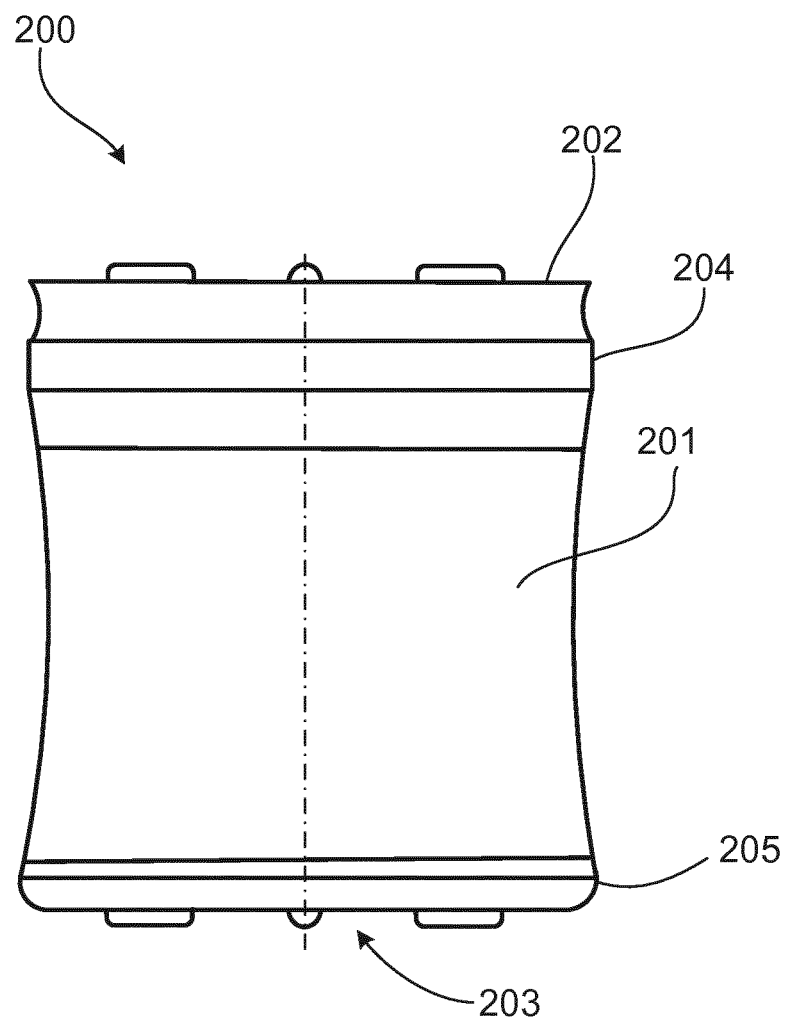
FIG. 2A is a side view of a stopper configured to be disposed in a cartridge of an injection device.
Figure 2B:
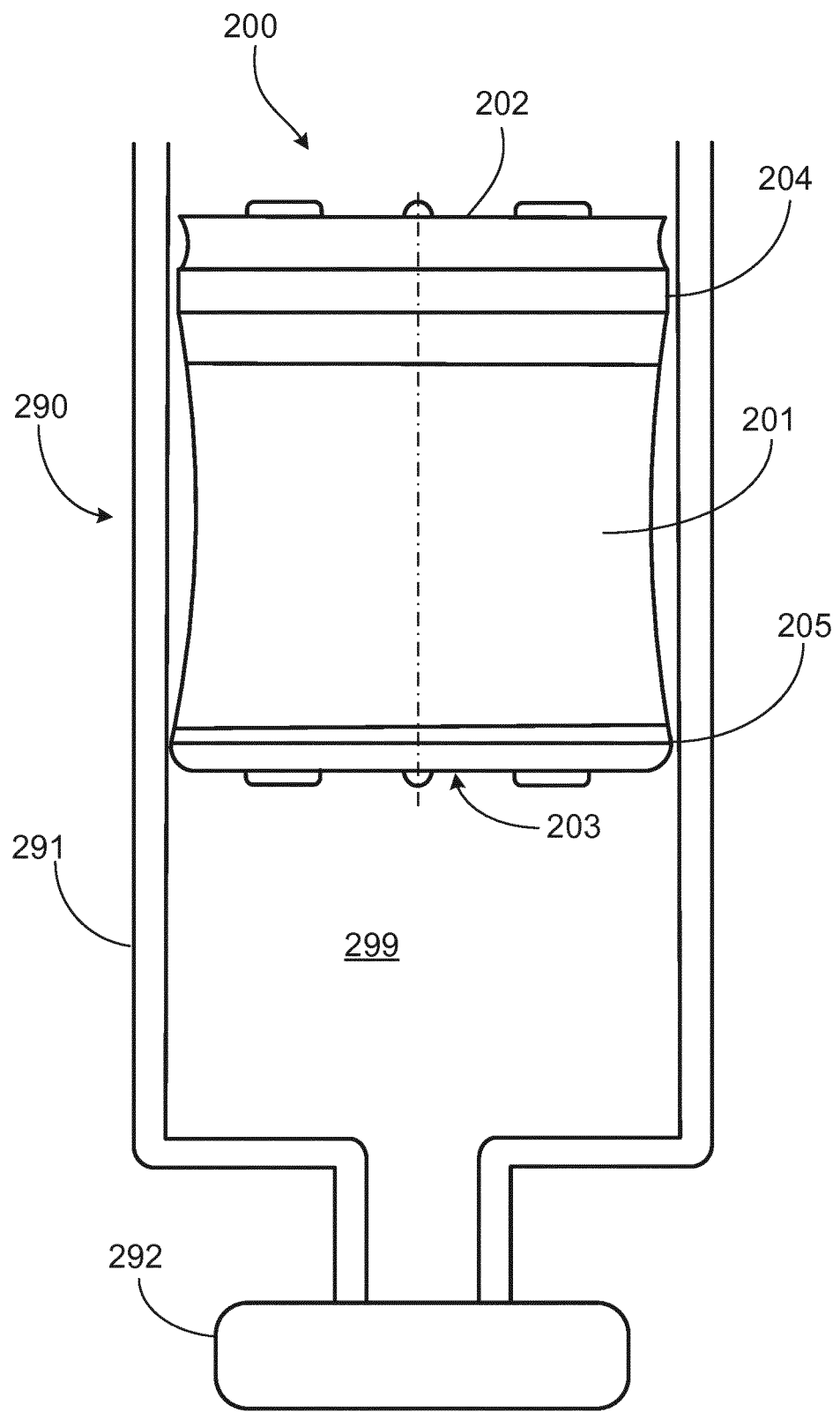
FIG. 2B is a cross sectional schematic of the stopper of FIG. 2A disposed in a cartridge.

FIG. 2A is a side view of a stopper 200 configured to be disposed in a cartridge of an injection device. The stopper 200 includes a proximal end 202 configured to be contacted by a plunger rod or other drive device in, for example, a syringe, injector, auto-injector, infusion pump device, or similar. The stopper also includes a distal end 203, which is a drug-contacting end of the stopper 200 and configured to be in contact with a medicament or similar inside of a cartridge or syringe into which the stopper 200 is disposed. The stopper 200 includes a body 201, which is later referred to as a shell when it defines an interior cavity configured to accept an insert, and an exterior surface of the body 201 includes proximal and distal sealing element 204,205 formed into the exterior surface as regions of a larger diameter, which are configured to sealingly interface with an inner surface of the cartridge of syringe into which the stopper 200 is disposed in order to seal the medicament into the cartridge or syringe and maintain that seal during movement of the stopper 200 along the inner surface, as illustrated in FIGS. 2B and 6B below. The sealing interface may form at least part of a sterile barrier within the cartridge 290 (FIG. 2B), which is required to preserve the sterility of the medicament to be delivered by an injection device.

FIG. 2B is a cross sectional view of a container closure system including the stopper 200 of FIG. 2A disposed in a cartridge 290. As shown in FIG. 2B, the stopper 200 is placed in the cartridge 290 such that the proximal and distal sealing element 204, 205 formed into the exterior surface of the body 201 of the stopper are in sealing engagement with an inner surface of a housing 291 of the cartridge 290. The cartridge 290 and stopper 200 enclose a volume 299 in the cartridge 290, and a distal end of the cartridge is closed by a cap 292, which may be, in some instances, a septum or port configured to deliver a medicament contained in the volume 299 when the stopper 200 is advanced in the cartridge 290.

Figure 3:
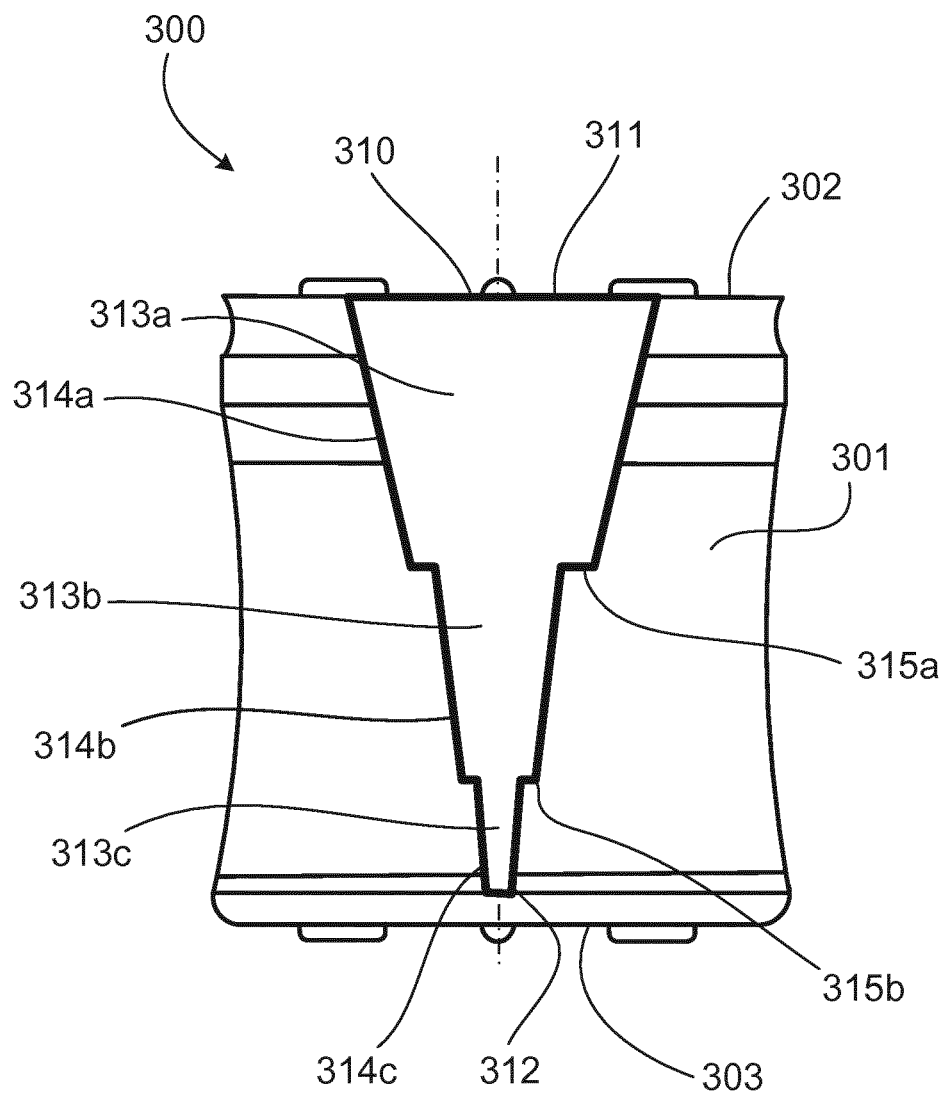
FIG. 3 is a cross-sectional view of a stopper with a stepped insert disposed in a cavity of the stopper.

FIG. 3 is a cross-sectional view of a stopper 300 illustrating a stepped insert 310 disposed in a cavity of a shell 301 of the stopper 300. The shell 301 includes a distal end 303 and a proximal end 302, with the cavity (not visible) formed in the proximal end 302, where the insert 310 is shown occupying the volume of the cavity. The insert includes a proximal end 311 being flush with the proximal end of the shell 301, and a distal end 312 located close to the distal end of the shell 301. The insert 310 is constructed of three main part 313*a-c*, which may be segments of a unibody construction, or individual parts joined or otherwise fixed together. Each of the main parts 313*a-c* of the insert 310 defines an exterior surface 314*a-c* having a conical taper decreasing towards the distal end 312, where discontinuities in the taper diameter between each of the exterior surfaces 314*a-c* create stepped surface 315*a*, 315*b* between the main segments 313*a-c*. The stepped surfaces 315*a*, 315*b* and the exterior surfaces 314*a-c* (and, for completeness, the distal end 312) are mirrored by the interior surface of the cavity of the shell 301 in order to interface the insert 310 in the cavity of the shell 301 as closely as possible. In this manner, the stepped surfaces 315*a*, 315*b* (illustrated as horizontal surfaces) of the insert 310 are abutting corresponding interface surfaces of the cavity, and, when a force (e.g., from a plunger rod) is applied to the proximal end 311 of the insert 310, a portion of the force is transferred to insert across the interface surfaces abutting the stepped surfaces 315*a*, 315*b*. In operation when a force is applied to the insert from a plunger rod to drive the stopper 300 in a cartridge, this stepped configuration reduces the radial component of the applied force that is created by the interaction of the conical exterior surfaces 314*a-c* and the cavity. Additionally, when the shell 301 is constructed from an elastomeric material, the force on the insert results in a reduced radial deflection of the shell 301 away from the insert 310 as the stepped surfaces 315*a*, 315*b* press axially (i.e., along a longitudinal axis of the stopper) against the interface surfaces of the cavity. As a result, movement of the insert 310 into the shell 301 is directly resisted by the shell 301, which enables the distal end 312 of the insert 310 to be located closer to the distal end 303 of the shell 301 without risking puncture of the distal end 303 by the distal end of the insert when the force is applied.

Figure 4:
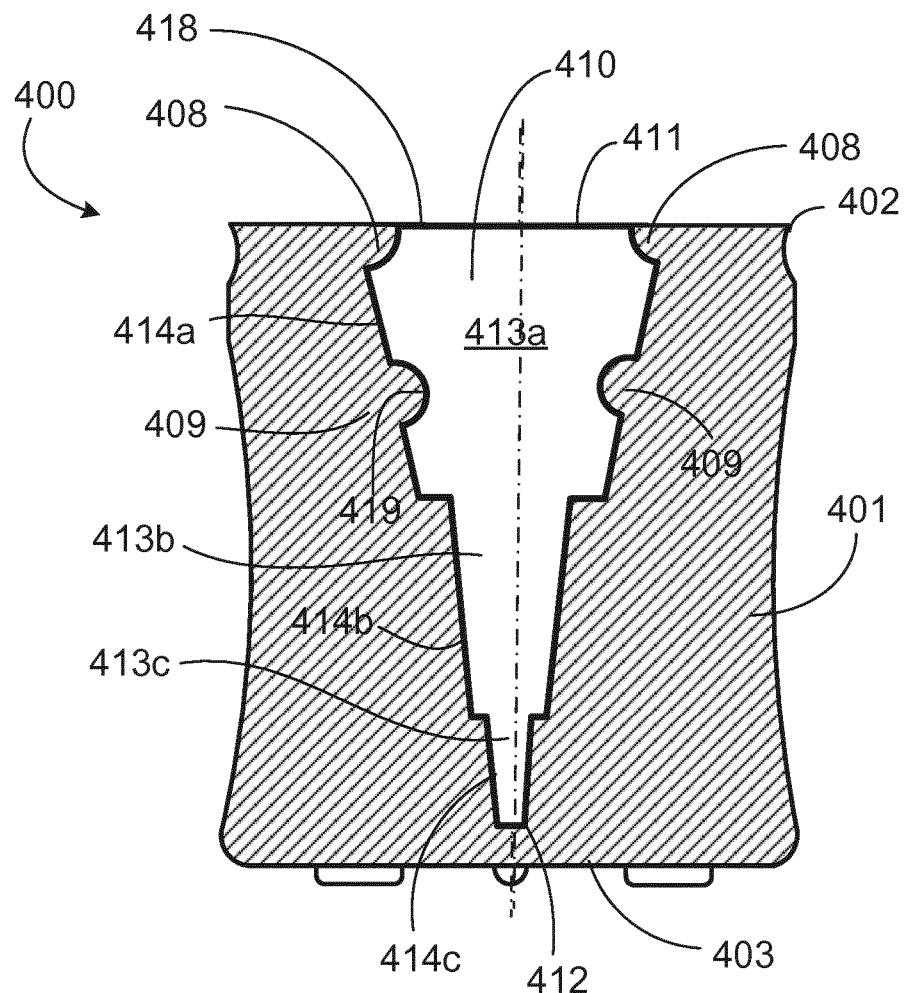
FIG. 4 is cross-sectional view of a stopper with an insert secured in a cavity of the stopper with snap-fit features.

FIG. 4 is cross-sectional view of a stopper 400 with an insert 410 secured in a cavity of a shell 401 of the stopper 400 with snap-fit features 408,409. The shell 401 includes a distal end 403 and a proximal end 402, with the cavity (not visible) formed in the proximal end 402, where the insert 410 is shown occupying the volume of the cavity. The insert includes a proximal end 411 being flush with the proximal end of the shell 401, and a distal end 412 located close to the distal end of the shell 401. The insert 410 is constructed of three main part 413*a-c*, which may be segments of a unibody construction, or individual parts joined or otherwise fixed together. Each of the main parts 413*a-c* of the insert 310 define an exterior surface 314*a-c* of a conical taper, and the proximal main part 413*a* has formed therein two grooves 418, 419 configured to mate with the snap-fit elements 408, 409 (e.g., circular or elliptical ring sections protruding into the cavity of the shell 401) and retain the insert 410 in the shell 401. In operation, the insertion of the insert 410 in the shell 401 deflects or otherwise deforms the snap-fit elements, which, in some instances, are constructed from an elastomeric material, until the snap-fit elements 408, 409 align with a corresponding groove 418, 419 in the insert. When aligned, the snap-fit elements 408, 409 relax radially inward into the grooves 418, 419 of the insert 401, and prevent easy removal of the insert 410 from the shell 401.

Figure 5:
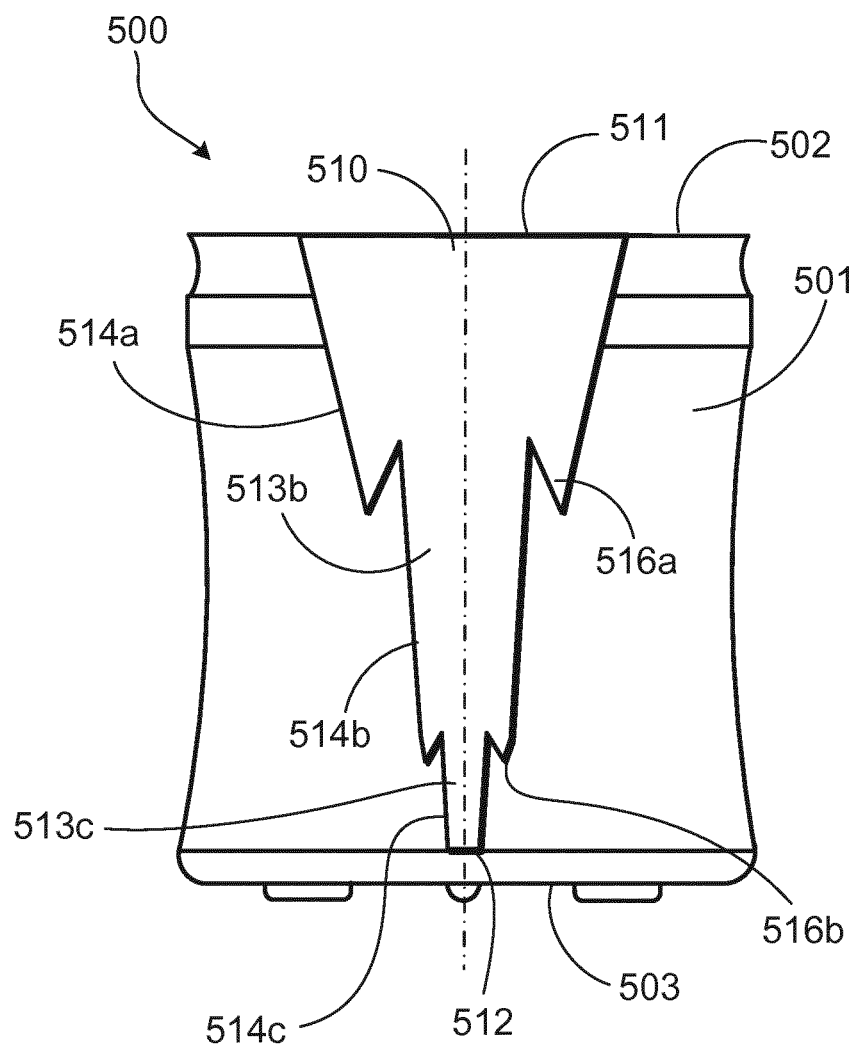
FIG. 5 is cross-sectional view of a stopper with an insert disposed in a cavity of the stopper.

FIG. 5 is cross-sectional view of a stopper 500 with an insert disposed in a cavity of a shell 501 of the stopper 500, where the cavity and the insert 510 defines acute angled projections that define angled interfaces surfaces 516,*b* configured radially retain the shell 501 to the insert 510. The shell 501 includes a distal end 503 and a proximal end 502, with the cavity (not visible) formed in the proximal end 502, where the insert 510 is shown occupying the volume of the cavity. The insert includes a proximal end 511 being flush with the proximal end of the shell 501, and a distal end 512 located close to the distal end of the shell 501. The insert 510 is constructed of three main part 513*a-c*, which may be segments of a unibody construction, or individual parts joined or otherwise fixed together. Each of the main parts 513*a-c* of the insert 510 defines an exterior surface 514*a-c* of a conical taper, where discontinuities in the taper diameter between each of the exterior surfaces 514*a-c* create inwardly stepped surfaces 516*a*, 516*b* between the main segments 513*a-c*. The inwardly stepped surfaces 516*a*, 516*b* and the exterior surfaces 514*a-c* (and, for completeness, the distal end 512) are mirrored by the interior surface of the cavity of the shell 501 in order to interface the insert 510 in the cavity of the shell 501 as closely as possible. In this manner, the inwardly stepped surfaces 516a, 516b of the insert 510 are abutting corresponding interface surfaces of the cavity, and, when a force (e.g., from a plunger rod) is applied to the proximal end 511 of the insert 510, a portion of the force is transferred to insert across the interface surfaces abutting the inwardly stepped surfaces 516a, 516b. This configuration reduces the radial component of the applied force that is created by the interaction of the conical exterior surfaces 514a-c and the cavity. Further, when the shell 501 is constructed from an elastomeric material, the inwardly stepped surfaces 516a, 516b prevent radial deflection of the shell 501 away from the insert 510. As a result, when a force is applied to the insert, movement of the insert 510 into the shell 501 is reduced compared with, for example, a contiguous conical insert, because a portion of the cavity 501 is trapped between the insert 510 and the inwardly stepped surfaces 516a, 516b, and this reduction enables the distal end 512 of the insert 510 to be located closer to the distal end 503 of the shell 501 without risking puncture of the distal end 503 by the distal end of the insert.

The materials selected for the shell 301, 401, 501 and the insert 310, 410, 510 are selected based on their hardness, elasticity, and their heat resistive or insulating properties. In some instances, the insert 310, 410, 510 is constructed from a material chosen to be able to be molded at a temperature below the maximum exposure temperature of any embedded electronic components, or a material able to be molded for a temperature and time and able to maintain the embedded electronic components below a minimum thermal budget of the electronic components. In some implementations, the shell 301, 401, 501 and the insert 310, 410, 510 are made of polymer materials with varying elastic properties. In some implementations, heat resistive coatings may also be applied to the insert 310, 410, 510 or to the shell 301, 401, 501 to increase heat resistance, such as, for example, a polytetrafluoroethylene (PTFE) coating. In some cases, the shell 301, 401, 501 is made of more rigid material which is selected to be compatible with the medicament e.g., PP, PE, COC, COP, PTFE or is made of elastomeric material, e.g. butyl rubber, halobutyl rubber, thermoplastic elastomer (TPE), silicone rubbers, polyurethane and the like at least at the distal end 303, 403, 503 which is in contact with the medicament.

The embedded electronic components may include, for example, a sensor, an energy source, a microcontroller, and a wireless transceiver. The sensor may be, in some instances, a sensor/transmitter device such as, for example, a piezoelectric device, an acoustic sensor, or an electromagnetic sensor. The sensor/transmitter may transmit a signal, such as, for example, an ultrasonic, acoustic, light, or other signal through the shell 301, 401, 501 and measure a response which may, in some instances, be used to determine the position of the stopper 200, 300, 400, 500 in a cartridge 114, 290 or if an injection of the syringe has occurred. In some instances, the response received by the sensor is provided to a controller (e.g. an embedded or an external microcontroller) which may receive the response and calculate a state of the cartridge 114, 290. The state of the cartridge 114, 290 may correspond to, in some instances, a fill level of medicament in the cartridge 114, 290 or a position of the stopper 200, 300, 400, 500. In some instances, the state of the cartridge 114, 290 enables a measurement of an injected dose of medicament.

In some instances, the energy source is a battery$_{[SZ1]}$, by any energy harvesting technologies which may load a capacitor or a solar source. The wireless transceiver may communicate with an external electronic device as well as with the sensor and energy source. The external electronic device, which may be the controller, may communicate data received from the sensor to an external database. The wireless transceiver may communicate using any known wireless communication technique including, for example Bluetooth, NFC, or radio frequencies.

The stoppers 300, 400, 500 of FIGS. 3-5 may be sterilized, for example, by using a moist heat sterilization process prior to the insertion of the insert 310, 410, 510. In a typical moist heat sterilization process, a completed stopper containing the insert would be sterilized at a temperature of approximately 105 to 130 degrees Celsius for between approximately fifteen and sixty minutes. In some instances, moist heat-sterilization includes saturated steam sterilization (e.g., at >121° C./20 min). In other instances, sterilization could also be done by irradiation (e.g., gamma, or e-beam) or by gas sterilization. However, batteries typically do not withstand high temperatures above 70° C. Thus, steam and high-heat sterilization processes may not be appropriate for inserts containing batteries. Further, electronics typically are sensitive to radiation. Thus, irradiation sterilization is also not right for the electronics. Suitable sterilization processes for the combination of rubber shell with insert containing sensitive electronics or batteries include gas processes, such as Ethylene Oxide (EtO), Chlorine Dioxide (ClO2) and Nitrogen Dioxide (NO2) sterilization. These processes are typically run at temperatures below 60° C. (EtO) and below 30° C. (NO2, ClO2).

In some instances, all components (e.g., shells 301, 401, 501 and inserts 310, 410, 510) would be assembled pre-sterilized in an aseptic manufacturing area prior to filling the container. The inserts could also be inserted into the stoppers after filling of the cartridge or syringe. This requires that the stopper without insert is sufficiently mechanically stable and rigid to achieve a tight seal for a filled container. For large sensor inserts, this can be best achieved with designing the stopper shell from more rigid material such as COP, COC and the like, whereas for smaller inserts a more elastomeric material like halobutyl rubber may be preferred. If the shell is to be sterilized without an insert, then steam sterilization at >121° C./20 min is preferred. An insert that is assembled into a prefilled and stoppered cartridge does not need to be sterilized, as it does not get into contact with the drug formulation.

Figure 6A:
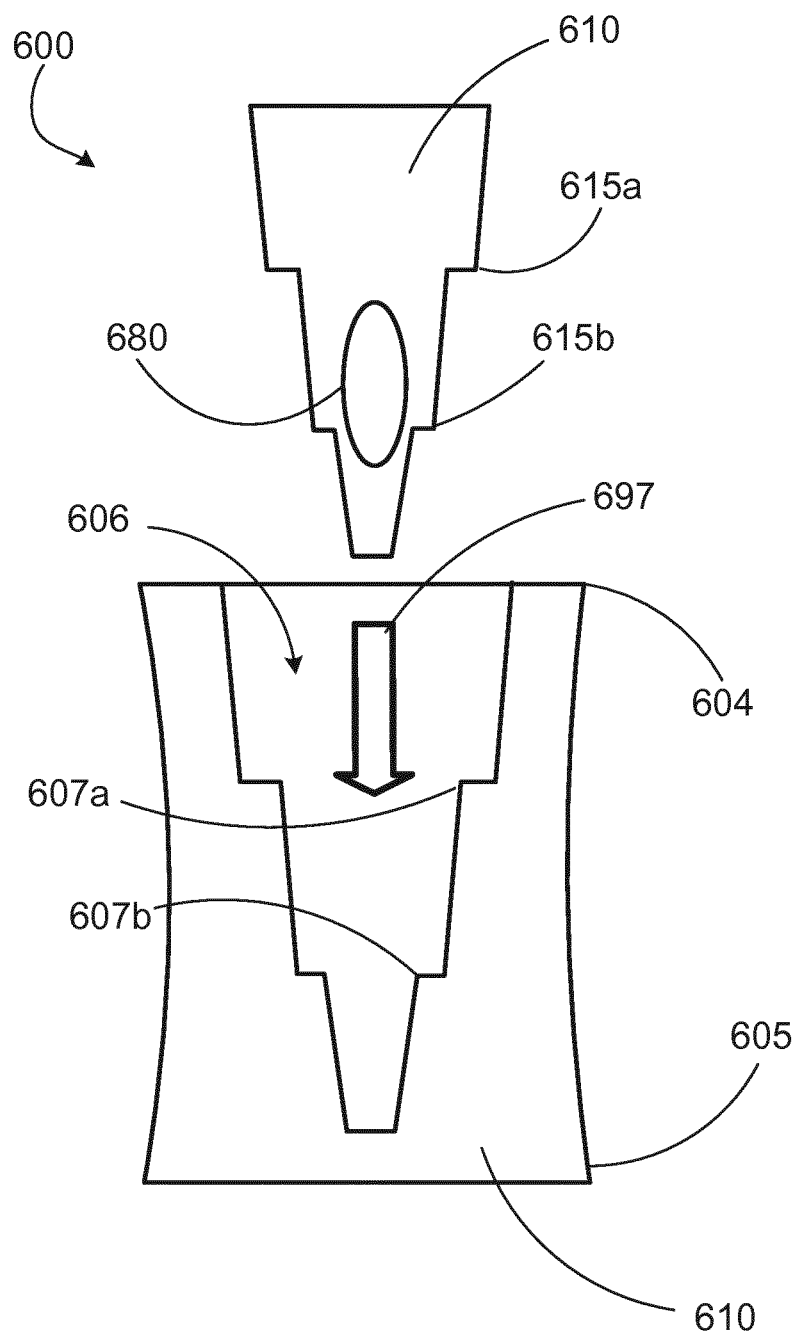
FIG. 6A is cross-sectional view of a stepped insert being inserted into a corresponding stepped cavity of a stopper.
Figure 6B:
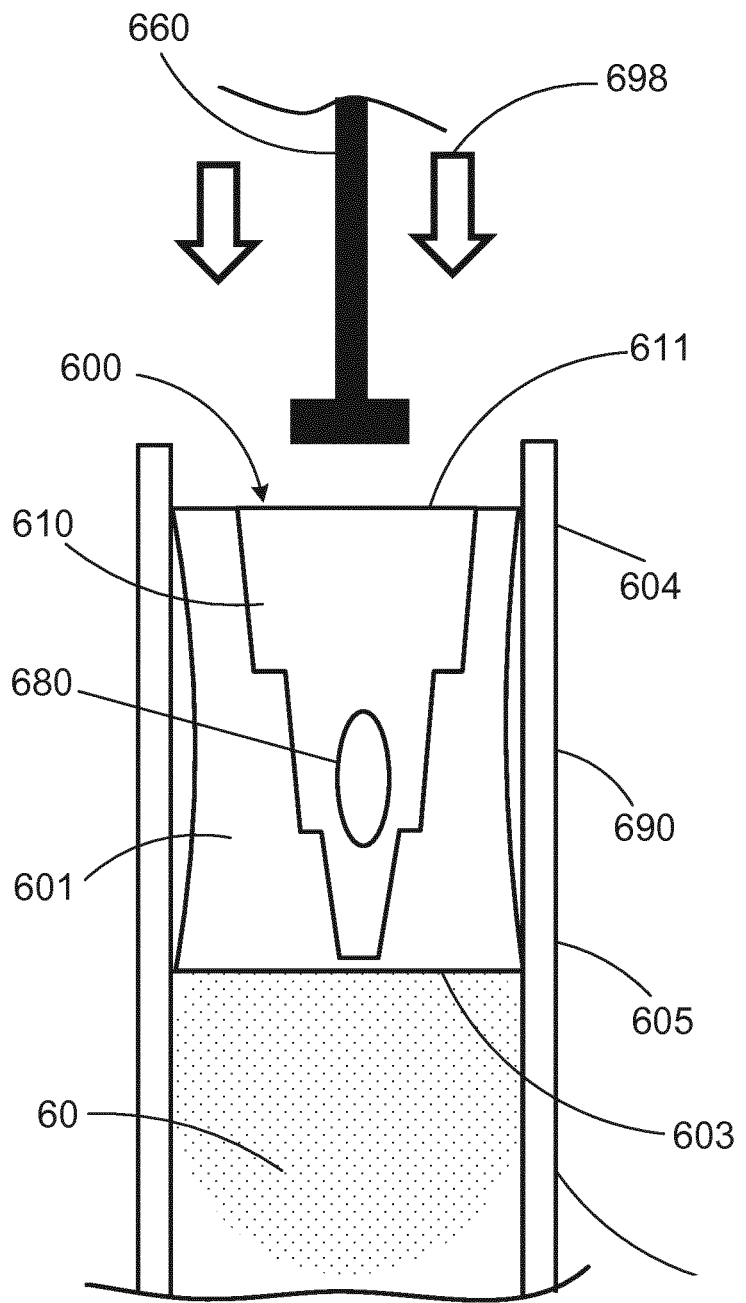
FIG. 6B is cross-sectional view the assembled stopper of FIG. 6A containing the insert before being driven by a plunger.

FIG. 6A is cross-sectional view of a stopper 600 being assembled by inserting an insert 610 into a cavity 616 formed by the shell 601. The cavity 616 includes an interior stepped profile that matches an exterior stepped profile of the insert 610. The cavity 606 includes interface surfaces 607a,b configured to abut corresponding stepped surfaces 615a,b, of the insert 610, as detailed above with respect to FIG. 3. During assembly, the insert 610 is inserted (as illustrated by arrow 697) into the cavity 606. Until the stepped surfaces 615a,b of the insert 610 abut the interface surfaces 607a,b. In some instances, the stopper 600 is an elastomeric container closure. The stopper 600 may be disposed inside of a cartridge (as shown in FIG. 6B), with proximal and distal sealing edges 604, 605 of the stopper 600 forming a seal around to contain a medicament in the cartridge. In some instances, an electronic component 680 (or electronic assembly) is contained in the insert 610 and contains, for example: a sensor, a power source (e.g., battery), a controller, a wireless communication module (e.g., IEEE 802.15, NFC, RF, IrDA), an acoustic module, memory, an on-off switch, a thermo-sensing element, a light-sensing element, or a pressure sensor. In some instances, the electronic component 680 includes an on-off switch configured to trigger the electronic component 680 by any suitable impact on the insert 610 of the stopper (e.g., by a force from a plunger rod or by a light signal).

FIG. 6B shows the stopper 600 before being driven by a plunger rod 660 into a cartridge 690. The plunger rod 660 (e.g., a plunger rod and head configured to contact the stopper 600) is, in some instances, driven by an actuator or drive mechanism of an injector (as shown in FIG. 1) having the cartridge 690, or is a plunger rod of a syringe where the cartridge 690 is the syringe housing. In operation, the plunger rod 660 is driven (as indicated by arrows 698) against the insert 610 and thereby applies a force to the shell 601 to move the entire stopper 600 into the cartridge 690 in order to drive a portion of the medicament 60 from the cartridge 690.

Figure 6C:
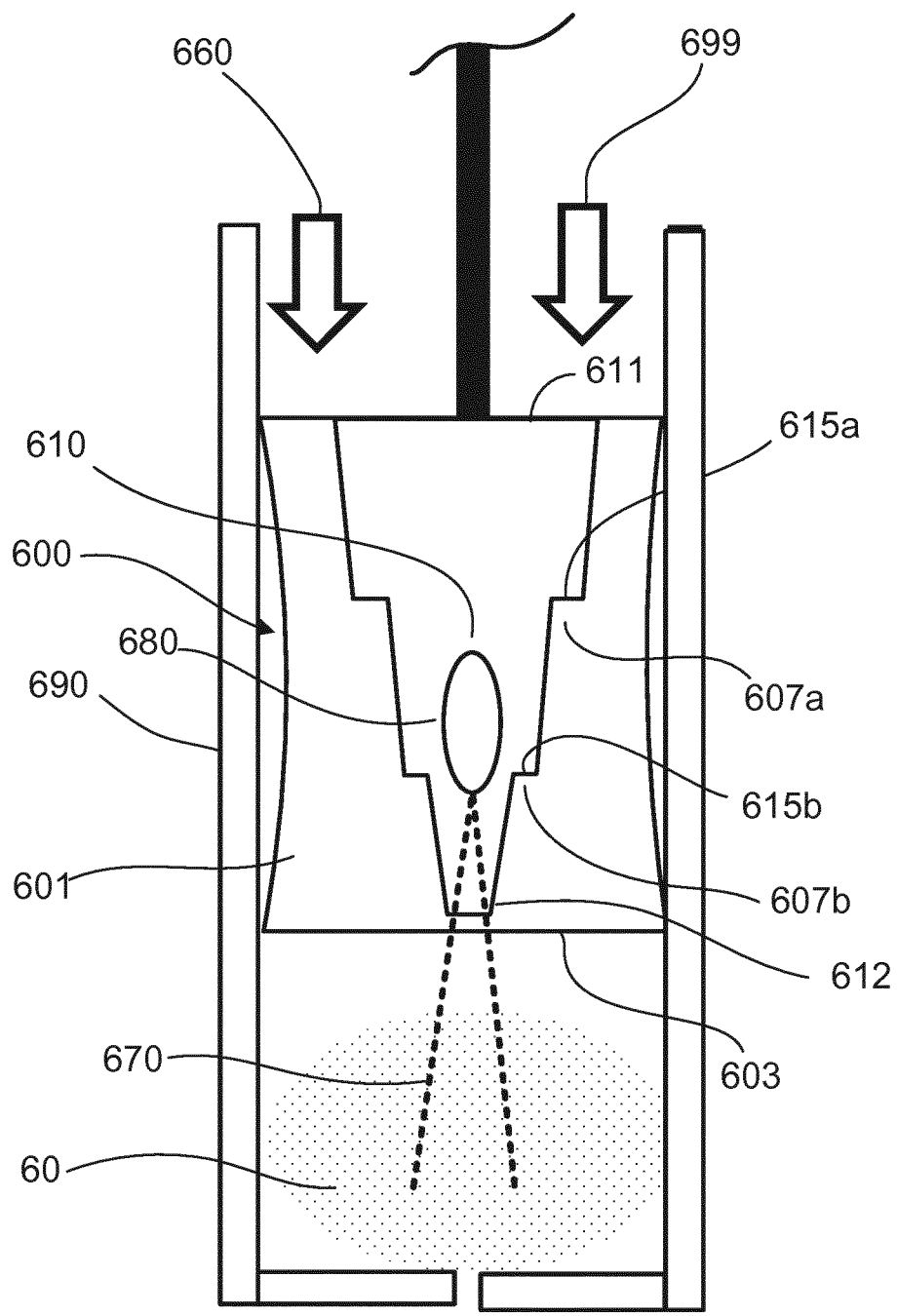
FIG. 6C is cross-sectional view the stopper of FIG. 6A during a sensing operating during or after being driven into the cartridge by the plunger

FIG. 6C is a cross-sectional view the stopper 600 of FIG. 6A during a sensing operating during or after being driven into the cartridge 690 by the plunger rod 660. FIG. 6C shows the plunger rod 660 contacting the insert 610 of the stopper 600 and having driven the stopper 600 into the cartridge 690 (as shown by arrows 699). In operation, the electronic component 680 may emit a sensing signal 670, which, in some instances, is responsive to the position of the stopper 600 in the cartridge 690 and enables the electronic component 680 to generate a signal indication of the movement of the stopper 600.

Described below are devices and methods for providing energy to electronic circuity in cartridge systems (for example, those disclosed herein) using energy harvesting to provide an alternative to standard batteries or as a supplement to batteries.

Aspects of the systems disclosed above enable medical injectors to employ 'smart' technologies by way of an attached of embedded electronic component (e.g., RFID, sensor) to give certain features to a cartridge of an injector device (e.g., of a pen-type injector). When integrating electronics into the stopper of a cartridge, one or more components may be active (e.g., a sensor to measure certain properties of the injector or cartridge) and require an energy source, which typically could be a battery. One alternative, as described below, is to use a means of energy harvesting as a power source replacement for a battery.

Figure 7:
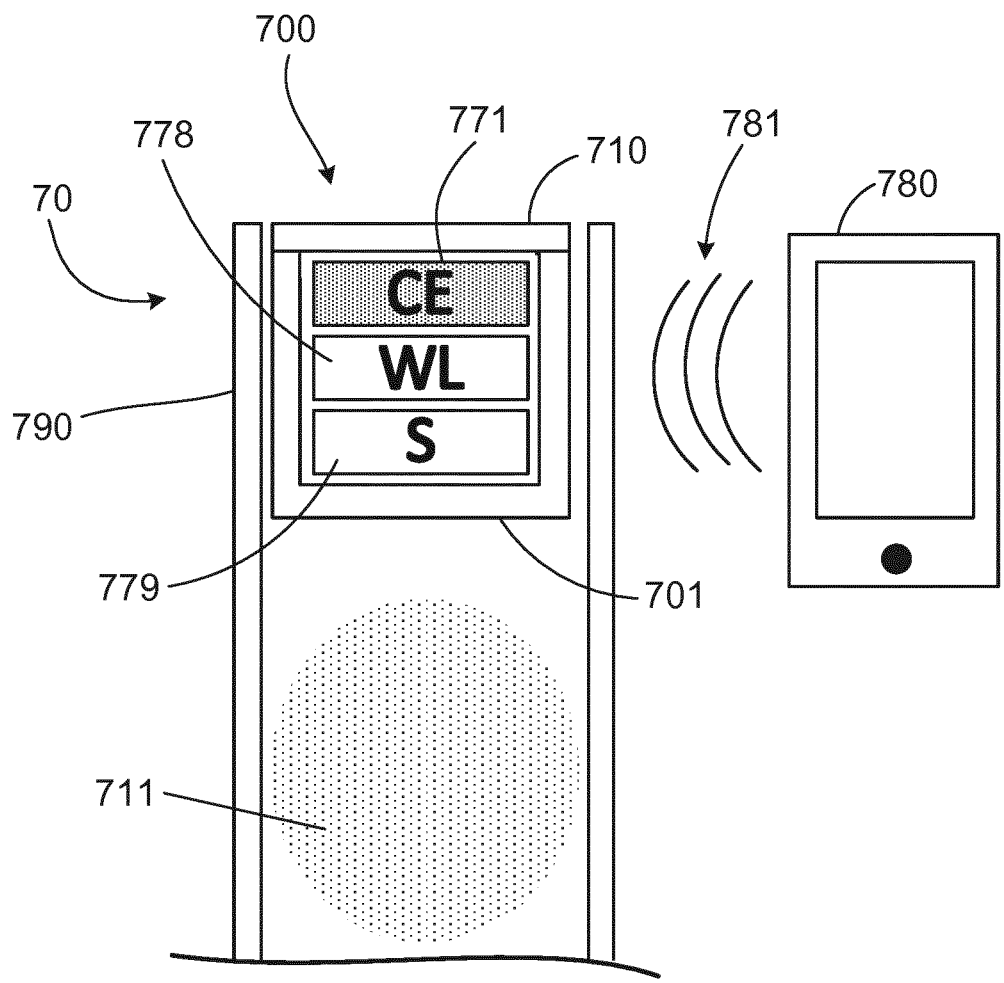
FIG. 7 is cross-sectional view of a stopper disposed within a cartridge and powered by a wireless system.

One example of an energy harvesting system in shown in FIG. 7, which is a cross-sectional view of a container closure system 70 including a stopper 700 disposed within a cartridge 790 and powered by a wireless system 780. The stopper 700 includes a shell enclosing a medicament 711 in the cartridge 790 and, in some instances, the shell 701 includes a plurality of sealing elements engaged to an inner surface of the housing 701. The stopper 700 also includes an insert 710 having an embedded electronics assembly 771, 778, 779. In operation, the electronics assembly 771, 778, 779 is, in some embodiments, integrated with or carried by the insert 710, whereby inserting the insert 710 into the shell 701 of the stopper 700 includes inserting the electronics assembly 771, 778, 779 into a cavity formed in the shell 701. The electronics assembly 771, 778, 779 includes a sensing device (S) 779, a wireless device (WL) 778, and a capacitive device (CE) 771.

In operation, the sensing device 779 is configured to sense the position of the stopper 700 within the cartridge 790, and the wireless device 778 is configured to communicate with an external electronic device (not shown) in order to communicate information from the sensor device 779. The capacitive device 771 is configured to provide electric power to the sensing device 779 and the wireless device 778 by way of wireless inductive charging from a wireless signal 781 located in proximity to the cartridge 790. In some embodiments, the capacitive device 771 includes capacitive circuitry that is configured to receive power wirelessly from, for example, a smartphone 780 via a nearfield communication protocol (NFC) signal 781, or by a typical wireless charging device with other means of inductive loading, in order to provide enough energy for initiating and performing measurements with the sensing device 779 in the cartridge 790 and for transmitting back the results using the wireless device 778.

Figures 8A, 8B:
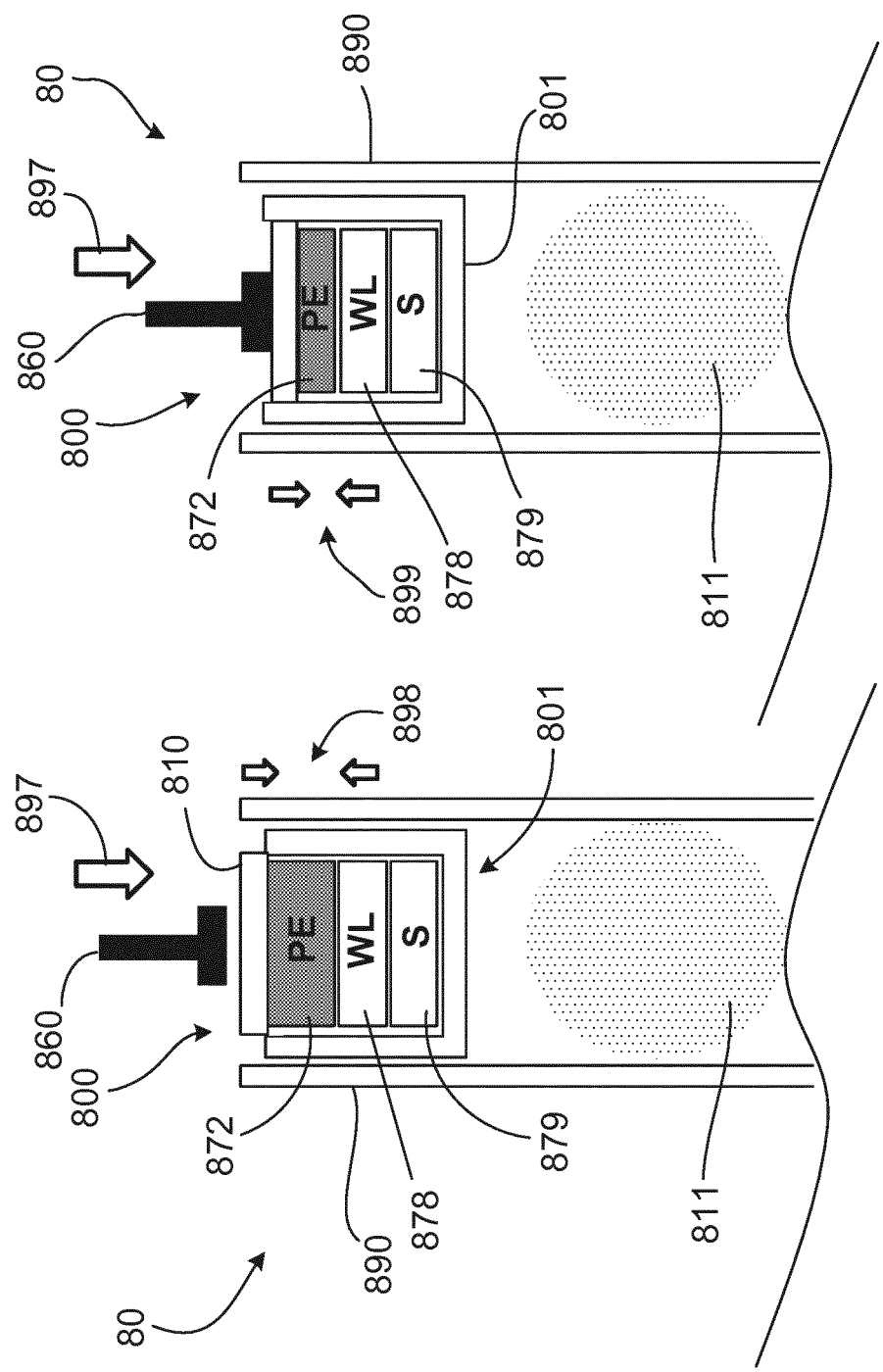
FIGS. 8A and 8B are cross-sectional views of a stopper disposed within a cartridge and powered by a piezoelectric system.

Another example of an energy harvesting system is the use of a piezo technology to collect energy from the mechanical forces occurring in between the stopper and plunger during, for example, injector handling or an injection operation, to provide enough energy for initiating and performing the measurement in the cartridge and for transmitting back the results. FIGS. 8A and 8B are cross-sectional views of a container closure system 80 including a stopper 800 disposed within a cartridge 890 and the stopper 800 includes a sensor insert 810 having electronics powered by a piezoelectric system. FIG. 8A shows the container closure system 80 being acted upon by a plunger 860 advancing (e.g., along arrow 897) to contact the insert 810 deposed in the stopper 800. The stopper 800 encloses a medicament 811 in the cartridge 890 where a shell 801 of the stopper 800 is sealingly engaged to an inner surface of the cartridge 890. The insert 810 is disposed in a cavity of the shell of the stopper 800, and the insert 810 includes an embedded electronics assembly 872, 878, 879. The insert 810 is configured to at least partially deflect under the force of the plunger 860 or otherwise enable a transfer for force from the plunger to a portion of the electronics assembly 872, 878, 879. In operation, the electronics assembly 872, 878, 879 is, in some embodiments, integrated with or carried by the insert 810, whereby securing the insert 810 to the stopper 802 includes inserting the electronics assembly 872, 878, 879 into the cavity of the shell of the stopper 800. The electronics assembly 872, 878, 879 includes a sensing device (S) 879, a wireless device (WL) 878, and a piezoelectric element (PE) 872.

In operation, the sensing device 879 is configured to sense the position of the stopper 800 within the cartridge 890, and the wireless device 878 is configured to communicate with an external electronic device (not shown) in order to communicate information from the sensor device 879. The piezoelectric element 872 is configured to provide electric power to the sensing device 879 and the wireless device 878 by way of transforming a portion of the force applied to the stopper 800 into electric energy. As shown in FIG. 8B, the piezoelectric element 872 is transformed from a position 898 of FIG. 8A to a deflected position 899 of FIG. 8B by the force applied to the insert 810 by the plunger 816 (during the motion indicated by arrow 897). The transformation of the piezoelectric element 872 from position 898 to the deflected position 899 absorbs energy and converts a portion of it to electric energy.

Another example of an integrated energy harvesting device is the inclusion of Peltier elements (PE) to convert the temperature differences between refrigeration (e.g., of the pen or injector during storage) and warming (e.g., exposure to room temperatures) into electric energy to provide enough energy for initiating and performing the measurement in a cartridge of the injector/pen and for transmitting back the results. FIGS. 9A and 9B are cross-sectional views of a container closure system 90 including a stopper 900 disposed within a cartridge 990, where the stopper 900 includes a Peltier thermoelectric device powering internal electronics devices. FIG. 9A shows a cartridge 990 being stored in a low temperature environment (e.g., 4° C.) and having a stopper 900 disposed in the cartridge 990 and plunger 960 positioned against an insert 910 disposed in a shell 901 of the stopper 900. The shell 901 of the stopper 900 encloses contain a medicament 911 in the cartridge 990 by being sealingly engaged to an inner wall of the cartridge 990. The insert 910 includes an electronics assembly 973, 978, 979, and the insert 910 or shell 901 is configured to at least partially transfer thermal energy to the electronics assembly 973, 978, 979. The electronics assembly 973, 978, 979 includes a sensing device (S) 979, a wireless device (WL) 978, and a thermoelectric element (TE) 973.

In operation, the sensing device 979 is configured to sense the position of the stopper 900 within the cartridge 990, and the wireless device 978 is configured to communicate with an external electronic device (not shown) in order to communicate information from the sensor device 979. The thermoelectric element 973 is configured to provide electric power to the sensing device 979 and the wireless device 978 by way of generating energy when the temperature of the thermoelectric element changes. As shown in FIG. 9B, the container closure system 90 is moved to a relatively higher temperature environment (e.g., 20° C.) and the thermoelectric element 973 is heated by absorbing thermal energy from the environment outside the container closure system 90 (during the temperature transition indicated by arrow 999). The absorption of thermal energy by the thermoelectric element 973 generates electric energy to power, for example, the sensing device 979 and the wireless device 978.

FIGS. 7-9 generally show inserts 710, 810, 910 of a generic shape in order to illustrated the embedded electronics components, but it is understand that inserts 710, 810, 910 may, in some instances, have shapes that include any of the stepped profile described herein.

Figure 10:
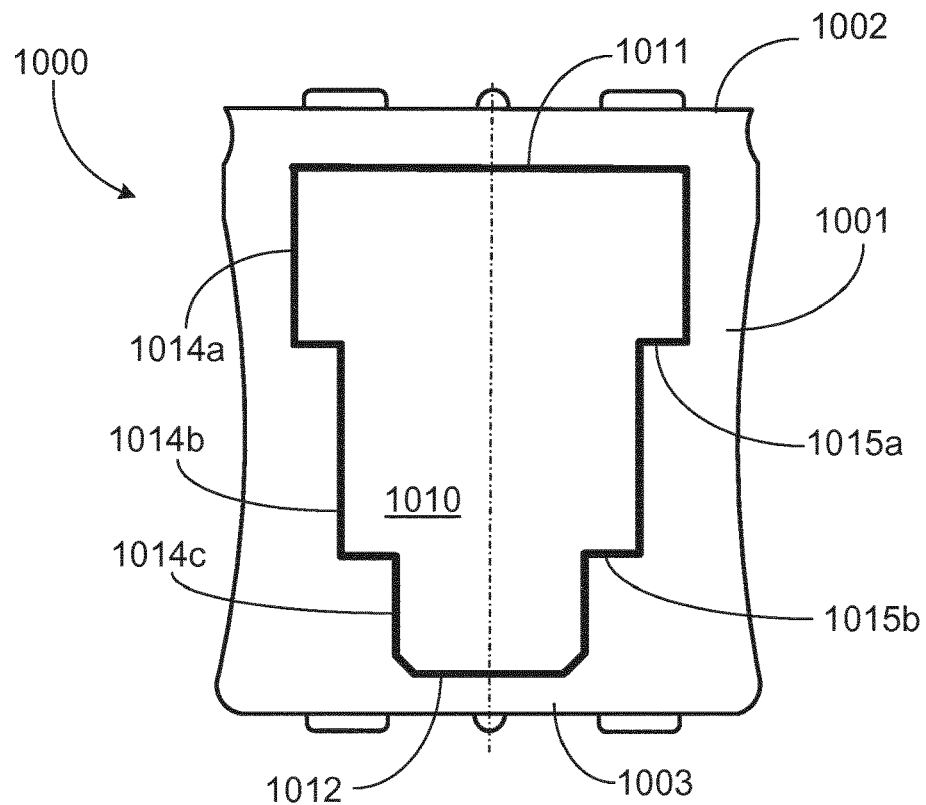
FIG. 10 is a side view of a stopper showing the outline of an insert disposed in the stopper, where the insert has a stepped profile.

FIG. 10 is a side view of a stopper 1000 showing the outline of an insert 1010 disposed in a cavity of a shell 1001 of the stopper 1000, where the insert 1010 has a straight stepped profile. The insert 1010 is disposed in the shell 1001 such that a proximal end 1011 of the insert 1010 is below the proximal end 1002 of the shell 1002, such that the insert 1010 is able to be hermetically sealed in the shell 1001 at the proximal end 1002. The hermetic seal protects the insert 1010 from contact with processing aids during washing and sterilization of the assembled stopper 1000. Further, the hermetic seal protects other stoppers in bulk shipping from contamination if e.g. a battery is leaking. Stoppers with a hermetically sealed insert can be easily washed, sterilized and thereafter processed in aseptic manufacturing areas. The shell 1001 includes a distal end 1003 and a proximal end 1002, with the cavity (not visible) formed in the proximal end 1002, where the insert 1010 is shown occupying the volume of the cavity. The insert includes a proximal end 1011 flush with the proximal end of the shell 1001, and a distal end 1012 located close to the distal end of the shell 1001. The insert 1010 defines straight (e.g., longitudinal) exterior surface segments 1014*a-c*, where discontinuities in between each of the exterior surface segments 1014*a-c* create stepped surfaces 1015*a*, 1015*b* between the exterior surface segments 1014*a-c*. The stepped surfaces 1015*a*, 1015*b* and the exterior surfaces 1014*a-c* (and, for completeness, the distal end 1012) are mirrored by the interior surface of the cavity of the shell 1001 in order to interface the insert 1010 in the cavity of the shell 1001 as closely as possible. In this manner, the stepped surfaces 1015*a*, 1015*b* (illustrated as horizontal surfaces) of the insert 1010 are abutting corresponding interface surfaces of the cavity, and, when a force (e.g., from a plunger rod) is applied to the proximal end 1011 of the insert 1010, a portion of the force is transferred to insert across the interface surfaces abutting the stepped surfaces 1015*a*, 1015*b*.

Figure 11:
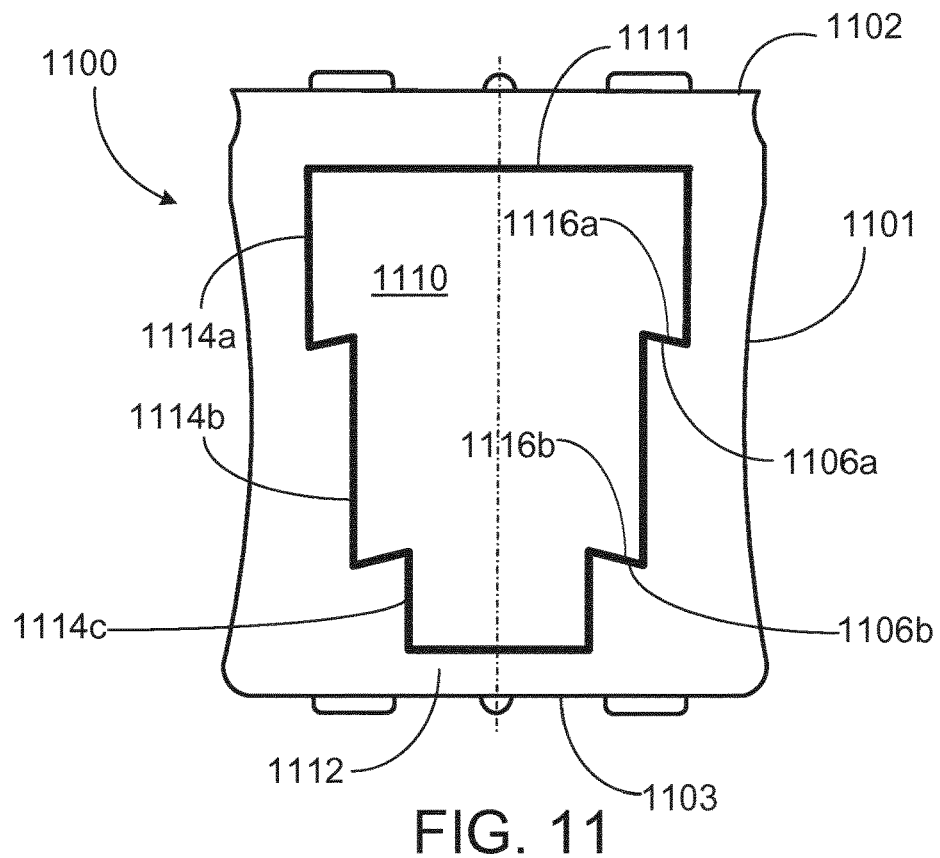
FIG. 11 is a side view of a stopper showing the outline of an insert disposed in the stopper, where the insert has a stepped profile with acute angles.

FIG. 11 is a side view of a stopper 1100 showing the outline of an insert 1110 in a cavity of a shell 1101 of the stopper 1100, where the cavity and the insert 1110 define acute angled projections that inwardly stepped surfaces 1116 configured to radially retain the shell 1101 to the insert 1110. The shell 1101 includes a distal end 1103 and a proximal end 1102, with the cavity (not visible) formed in the proximal end 1102, where the insert 1110 is shown occupying the volume of the cavity. The insert includes a proximal end 1111 being flush with the proximal end of the shell 1101, and a distal end 1112 located close to the distal end of the shell 1101. The insert 1110 defines straight (e.g., longitudinal) exterior surface segments 1114*a-c*, where discontinuities in between each of the exterior surface segments 1114*a-c* create inwardly stepped surfaces 1116*a*, 1116*b* between the exterior surface segments 1114*a-c*. The inwardly stepped surfaces 1116*a*, 1116*b* and the exterior surfaces 1114*a-c* (and, for completeness, the distal end 1112) are mirrored by the interior surface of the cavity of the shell 1101 in order to interface the insert 1110 in the cavity of the shell 1101 as closely as possible. In this manner, the inwardly stepped surfaces 1116*a*, 1116*b* of the insert 1110 are abutting corresponding interface surfaces 1106*a*, 1106*b* of the cavity, and, when a force (e.g., from a plunger rod) is applied to the proximal end 1111 of the insert 1110, a portion of the force is transferred to insert across the interface surfaces 1116*a*, 1116*b* abutting the corresponding inwardly stepped surfaces 1106*a*, 1106*b*. In addition, when the shell 1101 is constructed from an elastomeric material, the inwardly stepped surfaces 1116*a*, 1116*b* prevent radial (outward) deflection of the shell 1101 away from the insert 1110.

Figure 12:
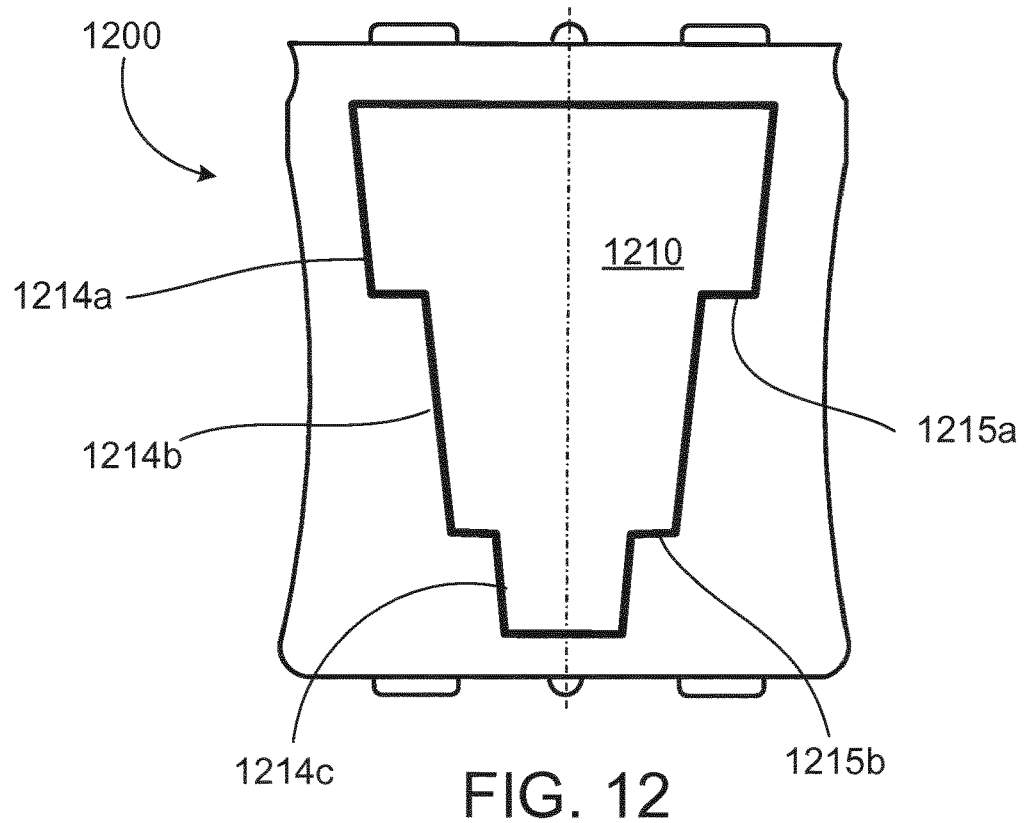
FIG. 12 is a side view of a stopper showing the outline of a tapered insert disposed in the stopper, where the insert has a stepped profile.
Figure 13:
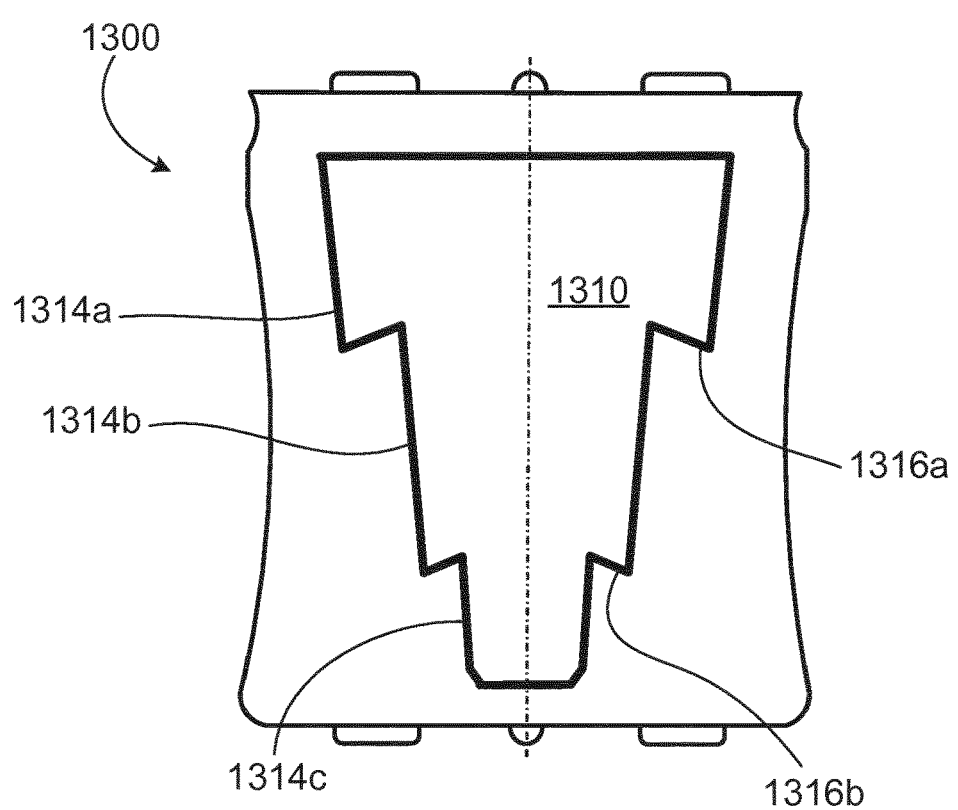
FIG. 13 is a side view of a stopper showing the outline of a tapered insert disposed in the stopper, where the insert has a stepped profile with acute angles.

FIG. 12 and FIG. 13 illustrate stoppers 1200, 1300 corresponding to the configurations of FIGS. 10 and 11 but with inserts 1210, 1310 having conical tapering exterior surfaces 1214*a-c* (FIG. 12), and 1314*a-c* (FIG. 13) forming the stepped surfaces 1215*a,b* and 1316*a,b*. In FIG. 13, the sloped interface surfaces 1316*a*, 1316*b* reduce the induced radial (outward) component of the applied force that is created by the interaction of the conical exterior surfaces 1314*a-c* and the cavity.

Figure 14:
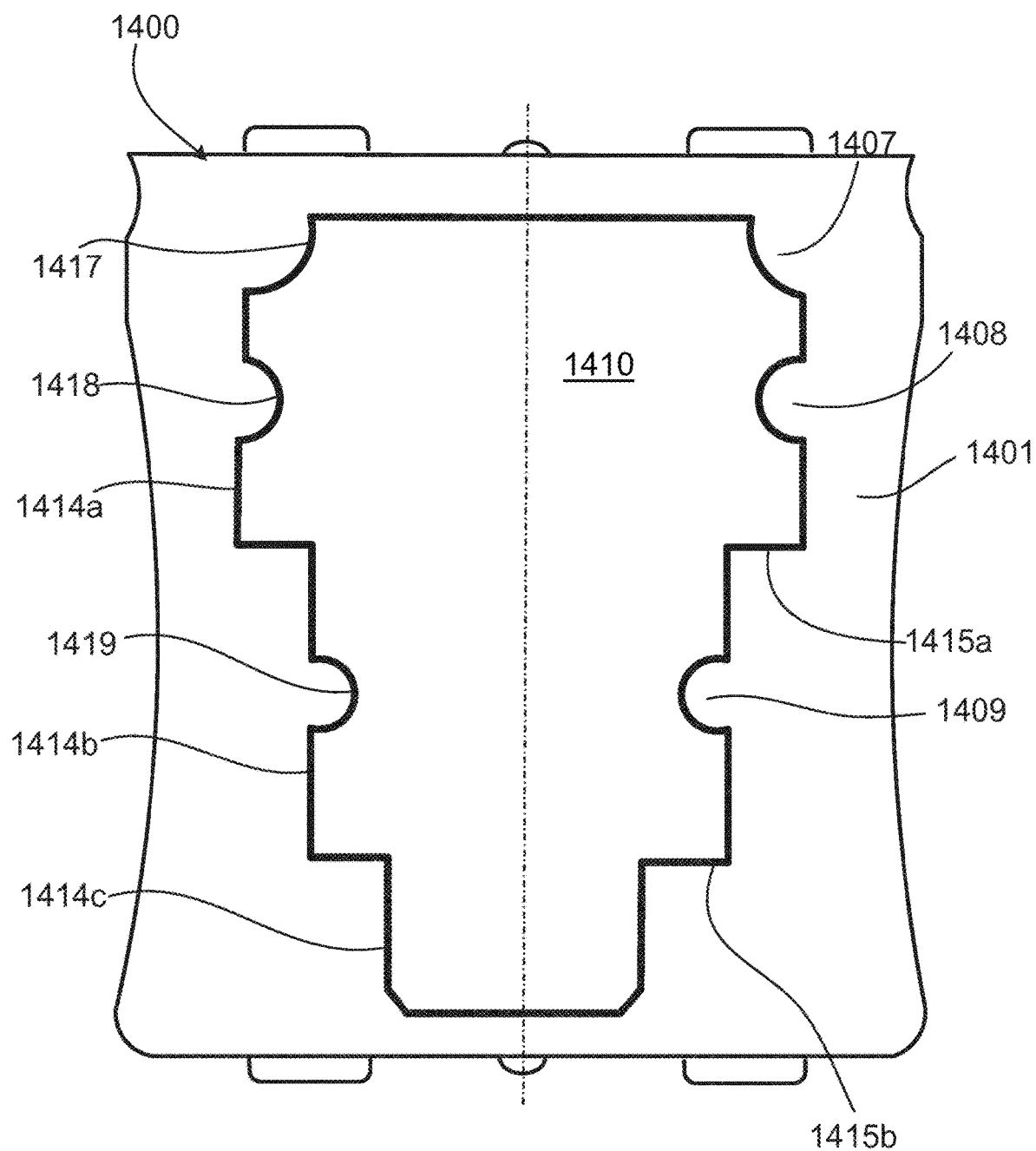
FIG. 14 is a side view of a stopper showing the outline of a insert disposed in the stopper, where the insert has a stepped profile with snap-fit features.

FIG. 14 is a side view of a stopper 1400 showing the outline of an insert 1410$_{[SL2]}$ disposed in a cavity of a shell 1401 of the stopper 1400, where the insert 1410 is secured in the cavity with snap-fit features 1417, 1418, 1419. The insert 1410 defines an exterior surface 1414*a-c* of a straight (i.e., longitudinal) profile, and the proximal an exterior surface 1414*a* and the middle exterior surface 1414*b* have formed therein three grooves 1417, 1418, 1419 configured to mate with the snap-fit elements 1407, 1408 (e.g., circular or elliptical ring sections protruding into the cavity of the shell 1401) and retain the insert 1410 in the shell 1401. In operation, the insertion of the insert 1410 in the shell 1401 deflects or otherwise deforms the snap-fit elements 1407, 1408, 1409, which, in some instances, are constructed from an elastomeric material, until the snap-fit elements 1407, 1408, 1409 align with a corresponding groove 1417, 1418, 1419 in the insert 1410. When aligned, the snap-fit elements 1407, 1408, 1409 relax radially inward into the grooves 1417, 1418, 1419 of the insert 1410$_{[SL3]}$, and prevent easy removal of the insert 1410 from the shell 1401.

Figure 15:
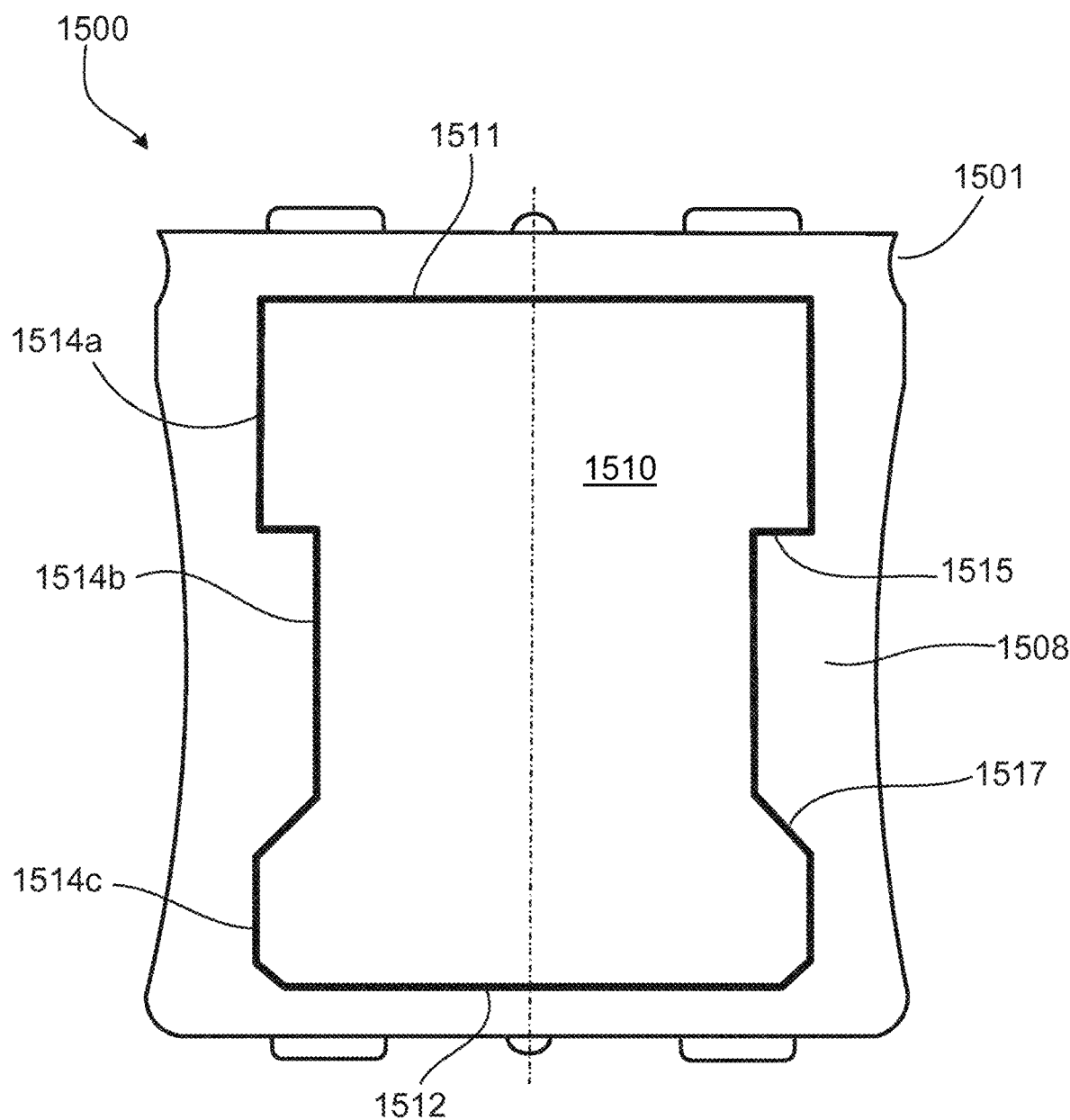
FIG. 15 is a side view of a stopper showing the outline of an insert disposed in the stopper, where the insert is fully inserted into the stopper.

FIG. 15 is a side view of a stopper showing the outline of a larger insert 1510$_{[SL4]}$ disposed in a shell 1501 of a stopper 1500, where the insert 1510 is fully inserted into the stopper 1500. The insert 1510 of FIG. 15 includes a larger distal end 1512 (i.e., as compared the inserts illustrated in the previous figures) such that the insert 1510 has a generally cylindrical shape from a proximal end 1511 to the distal end 1512. In this configuration, the insert 1510 is able to house a larger electronics assembly, which is able to have a larger portion at the distal end 1512 of the insert 1510$_{[SL5]}$ as compared with tapered shapes. The insert 1510 includes exterior surfaces 1514a-c, with a recessed exterior surface 1514b positioned between a proximal exterior surface 1514a and a distal exterior surface 1514c, each having a larger diameter than the recessed exterior surface 1514b. A stepped surface 1515 and an angled surface 1517 connect the recessed exterior surface 1514b with the adjacent surfaces 1514a, 1514c. In this way, the insert 1510 includes a combination of both a step design and a snap-fit design. The step design is present in the stepped surface 1515 between the proximal exterior surface 1514a and the recessed exterior surface 1514b, where the stepped surface 1515 configured to deliver a force to the shell 1501 as detailed above (see, for example, FIG. 3). Further, the recessed exterior surface 1514b and the adjacent stepped surface 1515 and angled surface 1517 define a groove for a snap-fit region 1508 of the shell 1501 to occupy and secure the insert 1510 to the shell 1505.

Figure 16A:
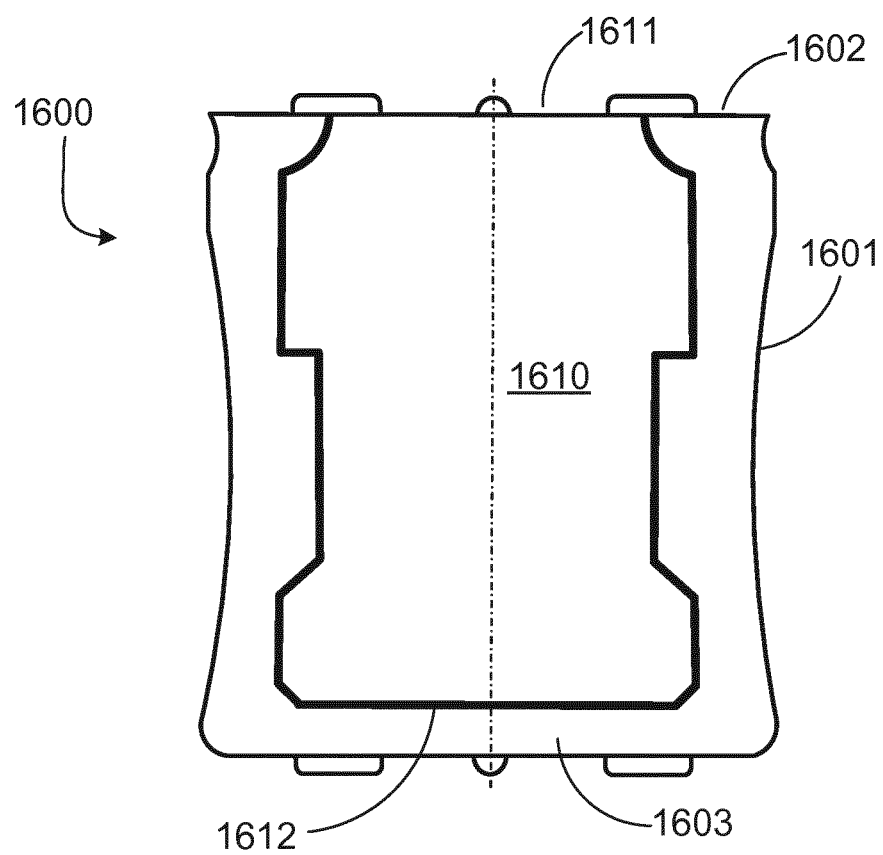
FIG. 16A is a side view of a stopper showing the outline of an insert disposed in the stopper, where the insert is flush with the stopper.

FIG. 16A is a side view of a stopper 1600 showing the outline of an insert 1610 disposed in a shell 1601 of the stopper 1600. The configuration of FIG. 16A is similar to that of FIG. 15, except that the proximal end 1611 of the insert 1610 is flush with the proximal end 1602 of the shell 1601. Because of the larger distal end thickness of the insert 1610 some examples include different constructions of the shell 1601 to reduce the possibility of air being trapped between the distal end 1612 of the insert 1610 and the shell 1601 after insertion, which can negatively affect the performance of the stopper 1600 disposed in a container or syringe by reducing the strength of the coupling between the insert 1610 and the shell 1601, which, in some instances, reduces the accuracy of the position of the shell 1601 in a container with respect to the position of a plunger rod contacting the insert 1610.

Figure 16B:
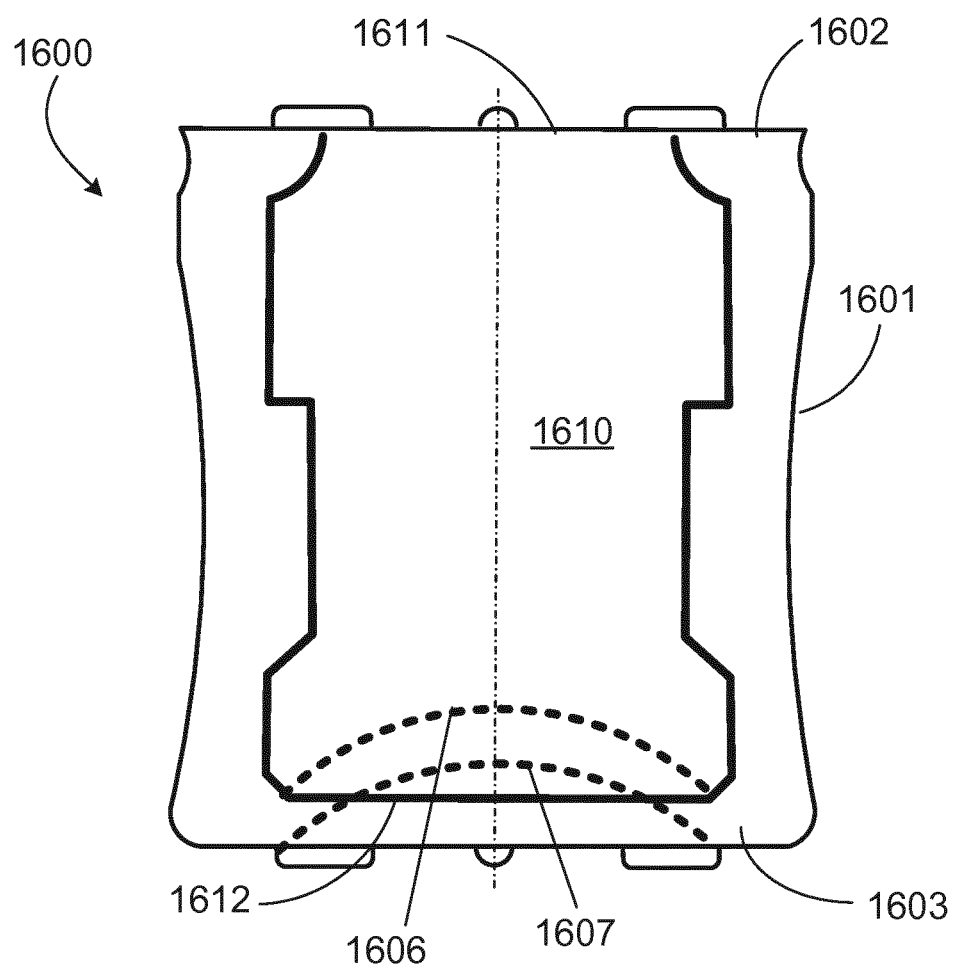
FIG. 16B is a side view of the stopper of FIG. 16 prior to insertion of the insert where the front part of the rubber has a concave shape towards the inner cavity.

FIG. 16B is a side view of the stopper of FIG. 16A modified to have a concave arch section 1607 forming a portion of the distal end 1603 of the shell 1601. This feature ensures that during assembly of the insert 1610 entrapped air is pushed away from the front end when the insert 1610 makes first contact to convex distal end 1606 of the cavity. The convex distal end 1606 will be pushed out by the insert to lay flat against the distal end 1612 of the insert 1610. With insertion of the insert 1610, the insert 1610 makes immediate contact with and deflects the convex distal end 1606 such that the concave arch section 1607 is deflected to form a flat exterior surface of the distal end 1603 and thus forming a designed shape of the stopper 1600. By providing that the insert 1610 makes contact with the convex distal end 1606, sensor functionality is improved, because it ensures a reliable location relationship between the sensor (e.g., in electronic device 680 of FIG. 6) in the insert 1610 and the stopper shell 1601 and, therefore, a reliable relationship between the sensor and any drug product filled into the cartridge outside the distal end 1603 of the stopper 1600. This improves the precision and predictability of sending and received a sensing signal though the distal end 1603 of the stopper 1600. In some instances, the exterior surface of the distal end 1603 is deflected to a non-flat shape upon insertion of the insert 1610, for example, a rounded surface.

Figure 17:
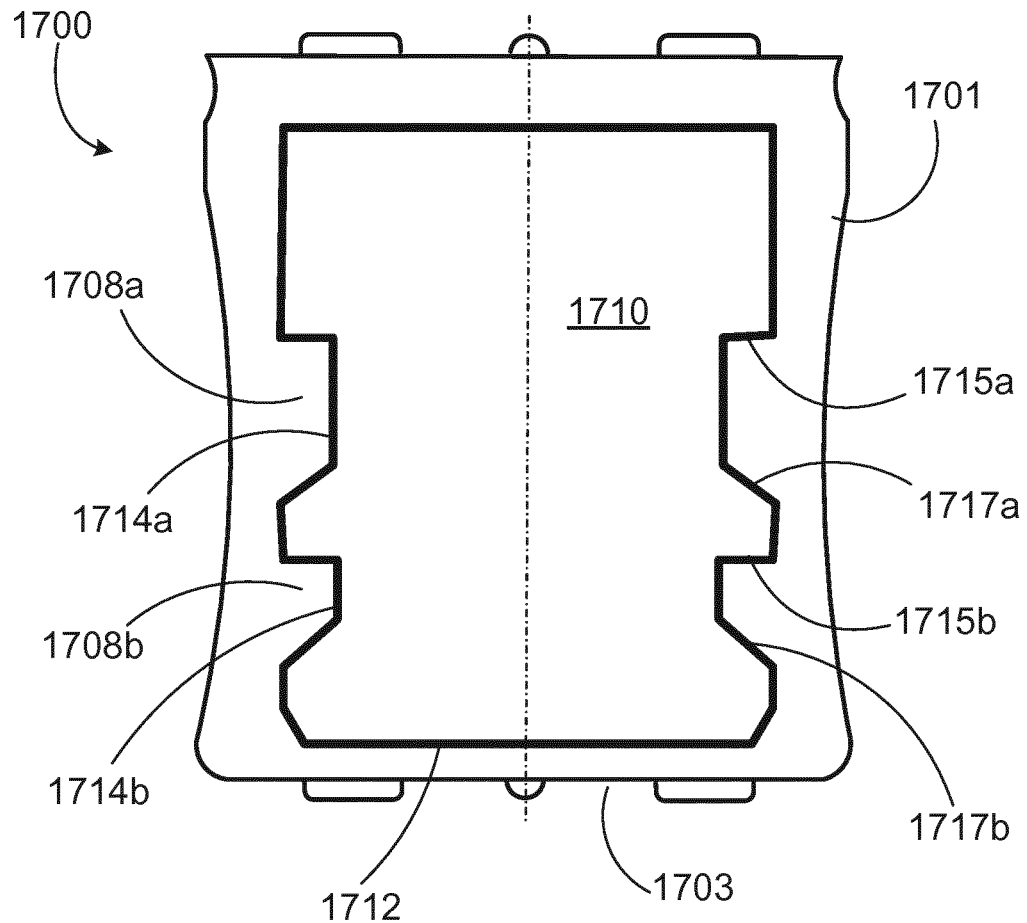
FIG. 17 is a side view of a stopper showing the outline of an insert disposed in the stopper, where the insert is sized to contain a larger electronics assembly.

FIG. 17 is a side view of a stopper 1700 showing the outline of an insert 1710 disposed in a cavity in a shell 1701 of the stopper 1700, where the insert 1710 is sized to contain a larger electronics assembly and is secured to the shell 1701 using two snap-fit elements. The insert 1710 includes two recessed exterior surfaces 1714a,b, which define two stepped elements 1715a,b, and two angled surfaces 1517, which are, together, configured to receive two corresponding snap-fit portions 1708a,b of the inner wall of the cavity of the shell 1701. In operation, the stepped elements 1715a,b distribute a portion of a force applied to the stopper 1700 to the shell and resist movement of a distal end 1712 of the insert 1710 into the cavity beyond a designed position with respect to a distal end 1703 of the shell 1701. During assembly, the snap-fit portions 1708a,b deflect to allow the insert 1710 to pass into the cavity of the shell 1701 and relax against the recessed exterior surfaces 1714a,b of the insert 1710 once the insert reaches its intended positioned in the shell 1701. In some instances, more than two snap-fit elements are used to secure the insert 1710 in the shell 1701.

Figure 18A:
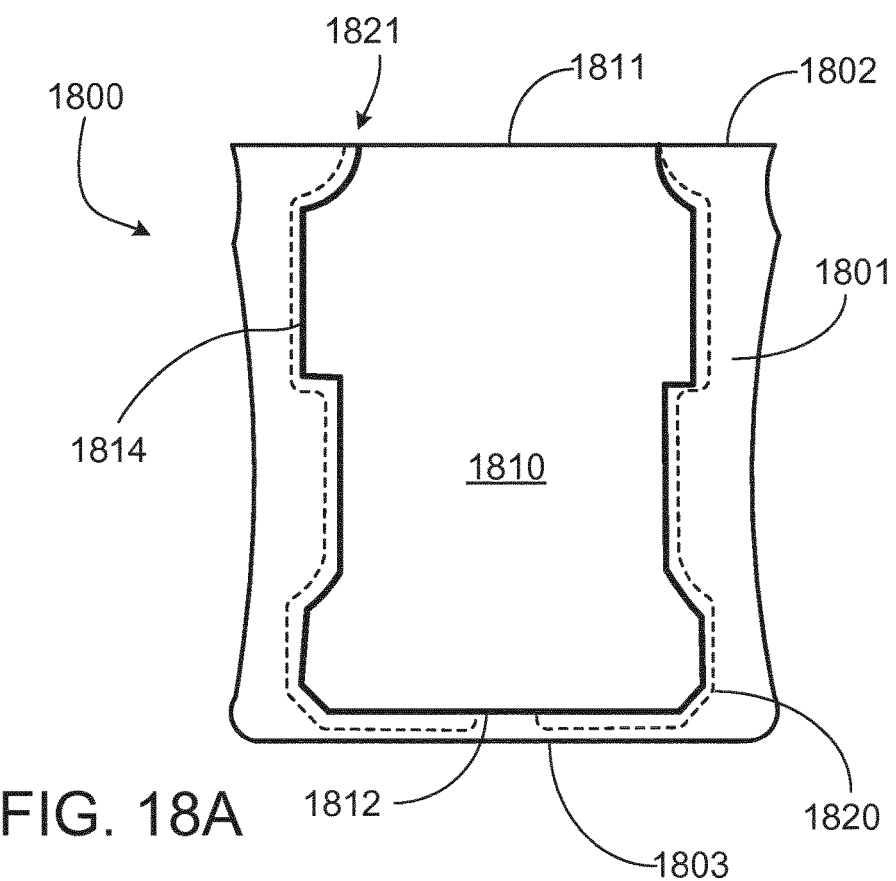
FIG. 18A is a cross-sectional view of a stopper with an insert deposed in a cavity of the stopper, where the cavity includes a vent channel.
Figures 18B, 18C:
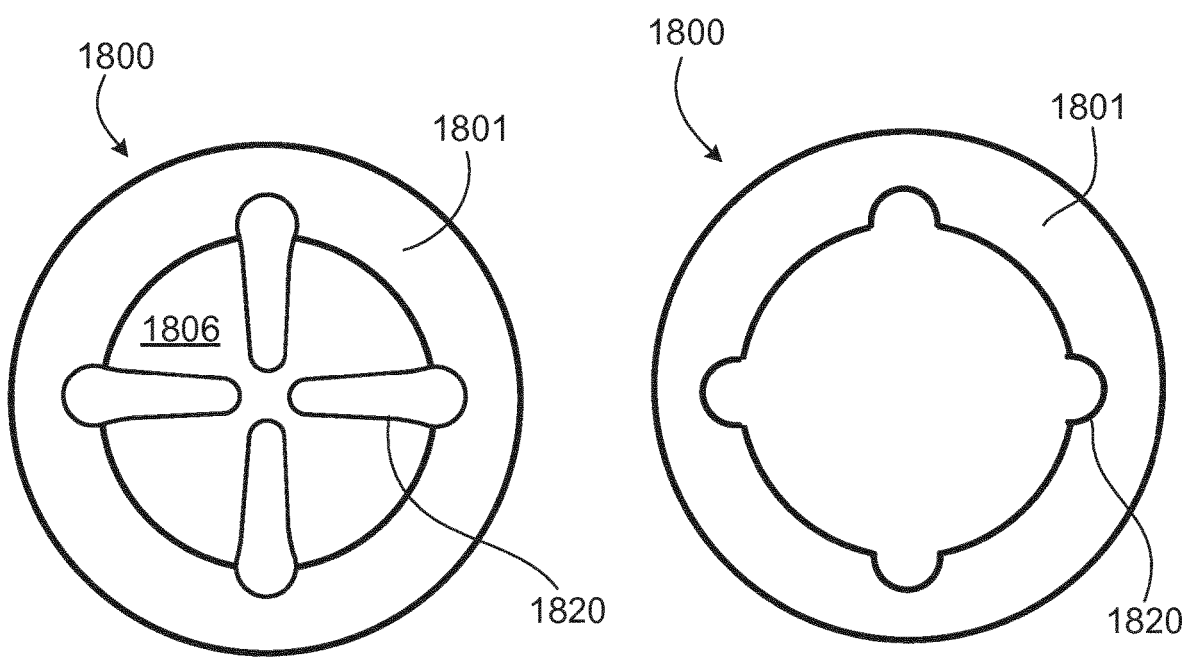
FIG. 18B is a top view of the stopper of FIG. 18A with the insert removed to view the vent channels in the cavity.
FIG. 18C is a cross-sectional view of the stopper of FIG. 18A showing vent channels though a middle portion of the shell.

FIGS. 18A and 18B are cross-sectional and top views, respectively of a stopper 1800 with an insert 1810 disposed in a cavity 1806 (shown in FIG. 18B of a shell 1801 of the stopper 1800, where the cavity 1806 includes a vent channel 1820. In operation, when the insert 1810 is inserted into the cavity 1806 air trapped between the distal end 1812 of the insert 1810 and the cavity 1806 is directed out of the stopper 1800 by passing through the vents 1820 to a space 1821 between the proximal end 1811 of the insert 1810 and the proximal end 1802 of the shell 1801 at the proximal end of the stopper 1800. FIG. 18C is a cross-sectional view of the stopper of FIG. 18A showing vent channels 1820 though a middle portion of the shell 1801.

Figure 19A:
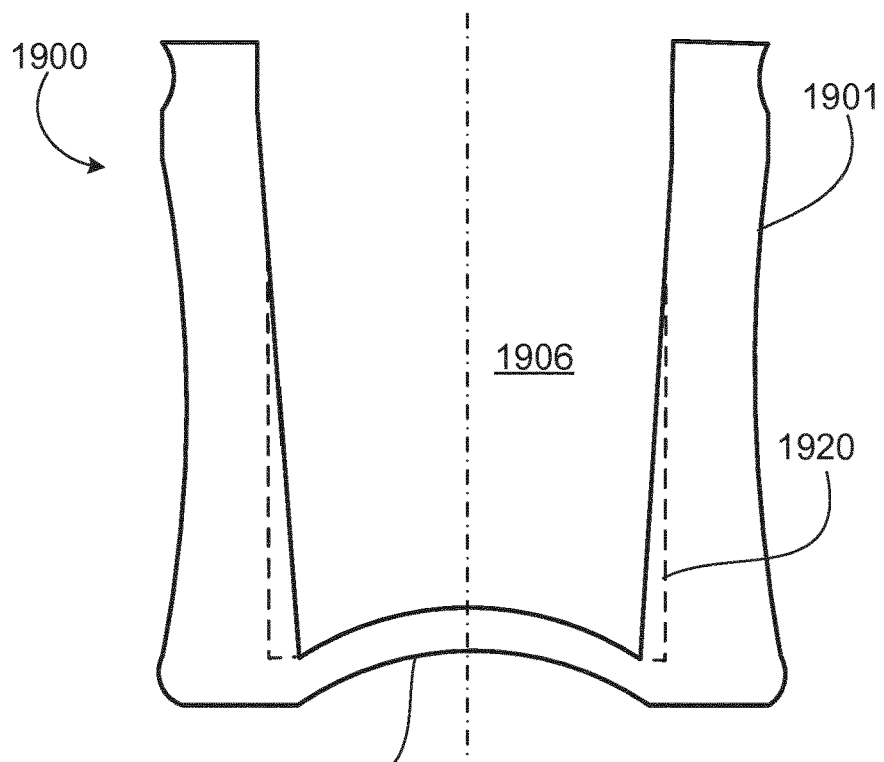
FIG. 19A is a cross-sectional view of a stopper with a conical cavity and an arched distal end.
Figure 19B:
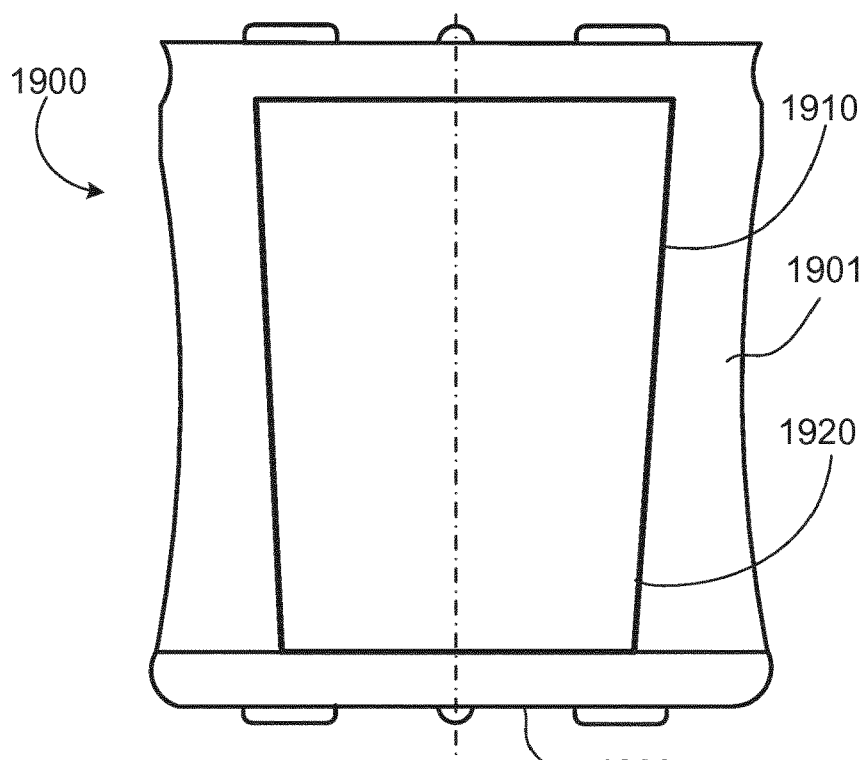
FIG. 19B is a side view of the stopper of FIG. 19A showing the outline of an insert disposed in the stopper, where the arched distal end is at a deflected position.

FIG. 19A is a cross-sectional view of a stopper 1900 with a conical cavity 1906 and an arched distal end 1903. The conical cavity 1906 is configured to accept a conical insert (1910 of FIG. 19B) and the arched distal end 1903 deflects to enable the insert 1910 to be fully inserted into the shell 1901. The arched distal end 1903 is flanked by vent channels 1920 in walls of the shell 1901, and the vent channels 1920 provide an egress for any air that may be trapped between the insert 1910 and the shell 1901 during insertion. In some instances, the vent channels 1920 do not extend fully to the open end of the cavity 1906, but instead provide small voids at the sides of the closed end of the cavity 1906 to enable to insert 1910 to be fully inserted without trapping air between the distal end of the insert 1910 and the shell 1901. In this way, the vent channels 1920 allow the distal end of the insert 1910 to contact the arched distal end 1903 and deflect the arched distal end 1903 during insertion until the distal end of the insert 1910 rests flush against the deflected arched distal end 1903, as shown in FIG. 19B. Also, the wall of the shell 1901 at the open end of the cavity may act as a flap valve against the outer wall of the insert 1910 to prevent ingress of expelled air back into space between the shell 1901 and the insert 1910.

FIG. 19B is a side view of the stopper 1900 of FIG. 19A showing the outline of the insert 1910 disposed in the stopper 1900, where the arched distal end 1903 is shown in a deflected position. In operation, the inwardly tapering sidewalls of the cavity 1906 deflect radially outward slightly to accept the insert 1910 when the arched distal end 1903 is deflected, but the walls maintain an inward taper to accept the conical shape of the insert 1910 and resist over-insertion of the insert 1910 into the cavity 1906 by being pressed against the walls of a container (not shown) in which the stopper 1900 is disposed and by the material properties of the arched distal end 1903 resisting a tensioned deformation as the insert 1910 pushes radially outward under a force from a plunger rod. While FIGS. 16, 19A, and 19B show a shell 1601, 1901 without step features, another embodiment of the present disclosure is a shell with an arch distal region and step features (of FIGS. 3-6C and 10-15) where the step features, for example, prevent over insertion of an insert into the cavity and/or retain the shell walls with sloped stepped features (where the sloped stepped features are shown in FIGS. 5 and 11). Any one or combination of the step features shown in FIGS. 3-6C and 10-15 are compatible with the arch configurations of FIGS. 16, 19A, and 19B.

Figure 20:
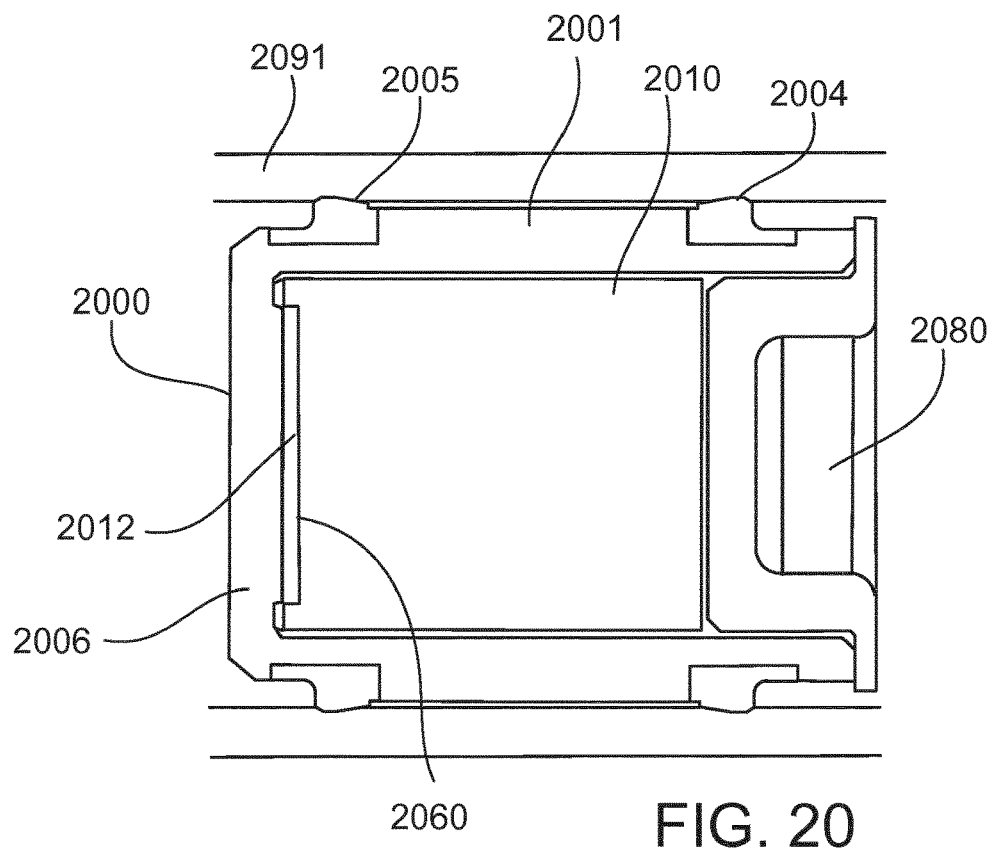
FIG. 20 is a cross-section illustration of rigid shell with in-molded seals where an insert is secured inside a cavity of the rigid shell with an adhesive.

FIG. 20 is a cross-section illustration of a stopper 2000 disposed in a container 2091. The stopper 2000 includes a rigid shell 2001 with in-molded seals 2004, 2005 and an insert 2010 secured inside a cavity of the rigid shell 2001 with an adhesive element 2060. The in-molded seals 2004, 2005 are arranged on the exterior surface of the rigid shell 2001 to create a sealing interface between the stopper 2000 and an inner surface of the container 2091. As an alternative to in-molded seals, also O-ring seals may be used (not shown). The stopper 2000 also includes a back-end closure cap 2080 inserted into the cavity behind the insert 2010 in order to seal the insert 2010 into the cavity of the stopper 2000. The adhesive element 2060 is arranged in the cavity of the rigid shell 2001 at the closed end such that the insert 2010 contacts the adhesive element 2060 when maximally inserted into the cavity. The adhesive element 2060, in some instances, is made from an adhesive material or includes an adhesive material on the exterior surfaces. The adhesive element 2060 is contacted by the insert 2010 when the insert 2010 is inserted into the cavity and affixes the insert 2010 to the closed end of the cavity of the rigid shell 2001. In some instances the adhesive element 2060 is contacted by the insert 2010 when the back-end closure cap 2080 is inserted into the cavity and contacts the insert 2010 such that the insert 2010 is driven forward against the adhesive element 2060 in order for the back-end closure cap 2080 to reach a position in the cavity where the back-end closure cap 2080 sealingly engages the rigid shell 2001. In some instances, the cavity of the rigid shell 2001 defines a front (i.e., distal) end 2006 defining a shape that corresponds to a shape of the distal end 2012 of the insert 2010. In some instances, the shape of the distal end 2006 of the cavity of the rigid shell 2001 is defined by the adhesive element 2060 extending into the cavity. In some instances, the adhesive element 2060 is attached to the insert 2010 prior to assembly with the rigid shell 2001.

Figure 21:
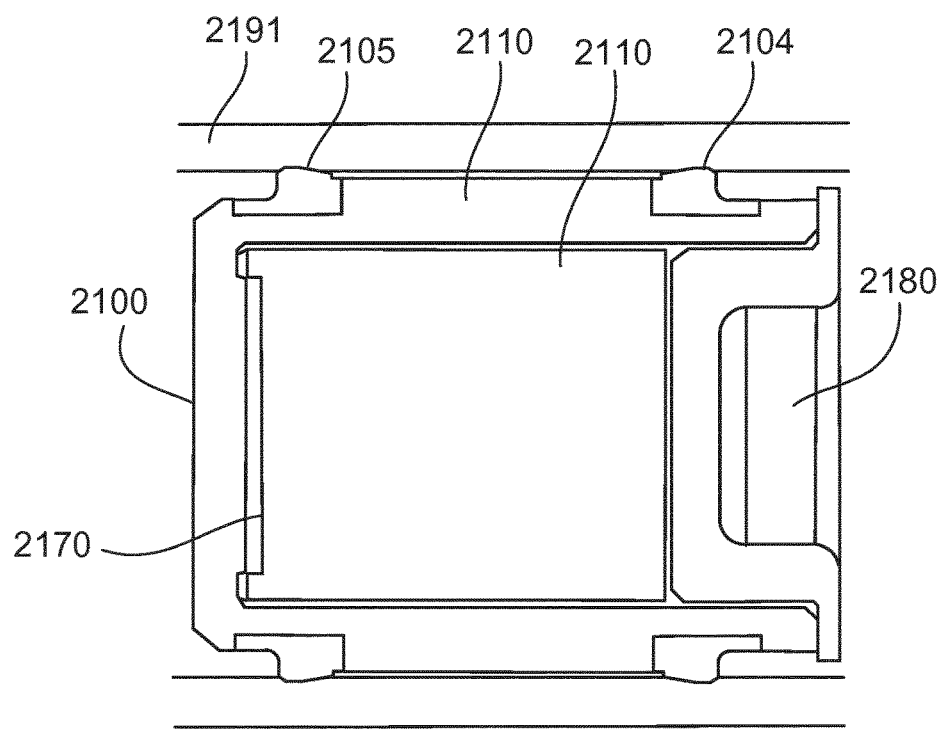
FIG. 21 is a cross-section illustration of rigid shell with in-molded seals where an insert is pressed into a deformable material in a cavity of the rigid shell.

FIG. 21 is a cross-section illustration of a stopper 2100 disposed in a container 2191. The stopper 2100 includes a rigid shell 2101 with in-molded seals 2104, 2105 and an insert 2110 pressed into a deformable element 2170 in a cavity of the rigid shell 2101. The stopper 2100 also includes a back-end closure cap 2180 inserted into the cavity behind the insert 2110 in order to seal the insert 2110 into the cavity of the stopper 2100. The deformable element 2170 is arranged in the cavity of the rigid shell 2101 at the closed end such that the insert 2110 contacts the deformable element 2170 when maximally inserted into the cavity. Alternatively, the deformable element 2170 may be attached to the insert 2110 prior to assembly into the rigid shell 2101. The deformable element 2170 is configured to be deformed by the insert upon insertion into the cavity and, in some instances, is made from an elastic and/or plastic deformable material (e.g., silicone, TPE material, glue or wax). In some instances, the deformable element 2170 defines a flat to convex shape made prior to being contacted and deformed by the insert 2110. The deformable element 2170 is contacted and deformed by the insert 2110 when the insert 2110 is pressed into the cavity and affixes the insert 2110 to the closed end of the cavity of the rigid shell 2101. In some instances the deformable element 2170 is contacted by the insert 2110 when the back-end closure cap 2180 is inserted into the cavity and contacts the insert 2110 such that the insert 2110 is driven forward against the deformable element 2170 in order for the back-end closure cap 2180 to reach a position in the cavity where the back-end closure cap 2180 sealingly engages the rigid shell 2101.

Figure 22:
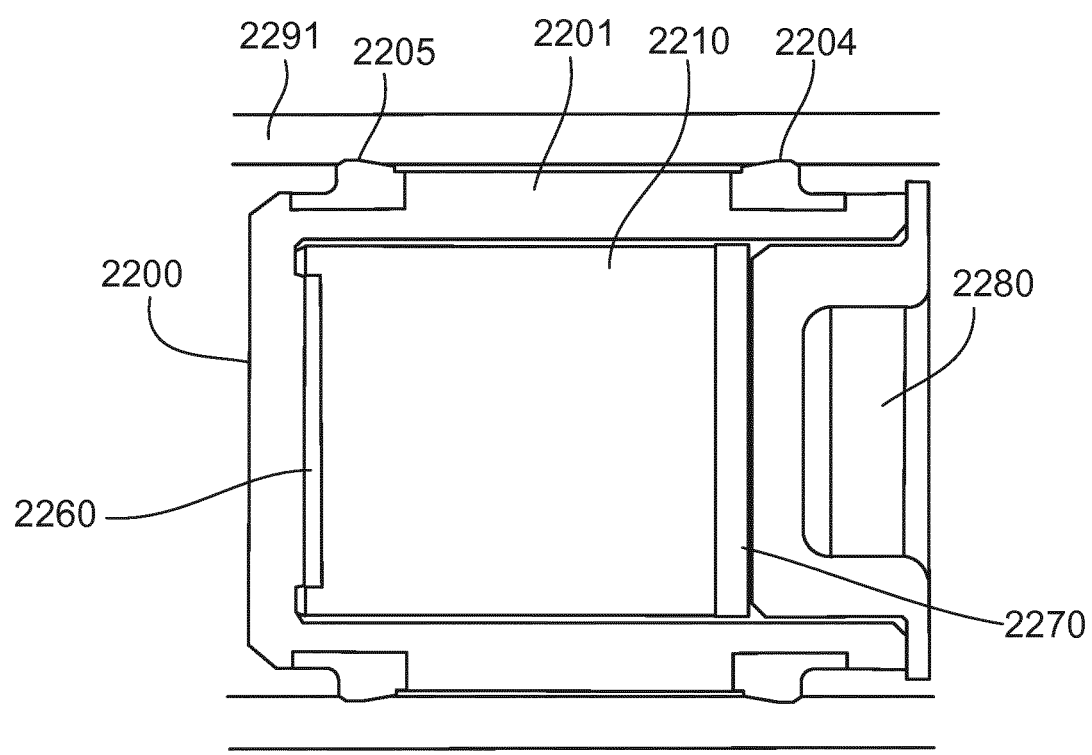
FIG. 22 is cross-section illustration of a rigid shell with in-molded seals where an insert secured inside a cavity of the rigid shell with an adhesive and a deformable material.

FIG. 22 is cross-section illustration of a stopper 2200 in a container 2291. The stopper 2200 includes a rigid shell 2201 with in-molded seals 2204, 2205 and an insert 2210 secured inside a cavity of the rigid shell 2201 with a deformable element 2270. The stopper 2200 also includes a back-end closure cap 2280 inserted into the cavity behind the insert 2210 in order to seal the insert 2210 into the cavity of the stopper 2200. The deformable element 2270 is arranged in the cavity of the rigid shell 2201 between the insert 2210 and the back-end closure cap 2280 such when the insert 2210 contacts the closed end of the cavity and the back-end closure cap 2280 is and driven forward against the deformable element 2270 to sealingly engage the rigid shell 2201, the deformable element 2270 is deformed between the insert 2210 and the back-end closure cap 2280. In some instances, similar to the arrangement of FIG. 20, an adhesive element 2260 is arranged in the cavity of the rigid shell 2201 at the closed end such that the insert 2210 contacts the adhesive element 2260 when the deformable element 2270 is pressed between the back-end closure cap 2280 and the insert 2210. In other instances, the insert 2210 directly engages the closed end of the cavity.

In some cases, the rigid shell 2001, 2101, 2201 is made of more rigid material which is selected to be compatible with the medicament e.g., PP, PE, COC, COP, PTFE or is made of elastomeric material, e.g. butyl rubber, halobutyl rubber, thermoplastic elastomer (TPE), silicone rubbers, polyurethane and the like at least at the distal end 2001, 2101, 2201 which is in contact with a medicament in the container 2091, 2191, 2291.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A stopper for use in a cartridge or a syringe of a medical device, the stopper configured to be disposed within a container closure system, the stopper comprising:

a shell comprising a closed end and an open end with sidewalls extending between the closed end and the open end along a longitudinal axis of the shell, the open end defining a cavity and the sidewalls defining an exterior surface sized and shaped to fit inside the container closure system; and an insert configured to be inserted into the cavity, the insert comprising a distal end and a proximal end and being sized and shaped to receive a force from a plunger rod and distribute the force to the shell to advance the shell into the container closure system, wherein the closed end of the shell in the cavity defines a convex surface that is curved into the cavity and configured to be contacted and deflected by the insert upon insertion of the insert into the cavity, wherein the closed end of the shell is made of an elastic and/or plastic deformable material, wherein the cavity comprises an interior step element, and wherein the insert comprises a corresponding step element configured to abut the interior step element and distribute at least a portion of the force from the plunger rod to the interior step element, and wherein the insert is constructed of a plurality of segments, whereby the segments decrease in size toward the distal end of the insert.

2. The stopper of claim 1, wherein the closed end of the shell defines an arch region defining the convex surface in the cavity and a concave exterior surface of the closed end of the shell, and wherein the arch region is configured to be deflected by the insert contacting the convex surface during insertion of the insert into the cavity.

3. The stopper of claim 2, wherein the cavity defines inwardly tapering sidewalls from the open end to the closed end of the shell, and wherein the inwardly tapering sidewalls are configured to maintain an inward taper when the arch region is deflected by the insert.

4. The stopper of claim 1, wherein the cavity defines a snap-fit feature extending into the cavity, the snap-fit feature configured to retain the insert in the cavity by being deflected or deformed by the insert during insertion of the insert into the cavity until the snap-fit feature relaxes into a corresponding depression in the insert, and wherein an exterior surface of the insert defines the corresponding depression being sized and positioned to accept the snap-fit feature.

5. The stopper of claim 1, wherein the corresponding step element is sized and positioned to retain the interior step element and resist radial deflection of the interior step element by the force applied to the insert.

6. The stopper of claim 1, wherein the interior step element defines a first interface surface, and wherein the corresponding step element defines a second interface surface, and wherein the first interface surface abuts against the second interface surface when the insert is inserted into the shell.

7. The stopper of claim 6, wherein the first interface surface and the second interface surface define acute angles about the closed end of the shell.

8. The stopper of claim 1, wherein the insert defines a conically tapering exterior surface configured to enable venting of air in the cavity around the exterior surface of the insert during insertion of the insert into the cavity.

9. The stopper of claim 1, wherein the insert comprises an electronic device having a sensor configured to generate a sensing signal, wherein the closed end of the shell is configured to allow the sensing signal to pass therethrough.

10. The stopper of claim 9, wherein the sensor is configured to be responsive to a position of the stopper in the container closure system.

11. The stopper of claim 1, wherein the cavity comprises at least one venting channel extending from the closed end of the shell toward the open end of the shell, the at least one venting channel being sized and positioned to enable air and/or fluid in the cavity to be expelled through the at least one venting channel during insertion of the insert into the cavity.

12. The stopper of claim 11, wherein the at least one venting channel extends only partially toward the open end of the shell.

13. A container closure system comprising:
a cartridge or a syringe comprising a housing; and
a stopper, comprising:
a shell comprising a closed end and an open end with sidewalls extending between the closed end and the open end along a longitudinal axis of the shell, the open end defining a cavity and the sidewalls defining an exterior surface sized and shaped to fit inside the container closure system; and
an insert configured to be inserted into the cavity, the insert comprising a distal end and a proximal end and being sized and shaped to receive a force from a plunger rod and distribute the force to the shell to advance the shell into the container closure system,
wherein the closed end of the shell in the cavity defines a convex surface that is curved into the cavity and configured to be contacted and deflected by the insert upon insertion of the insert into the cavity,
wherein the closed end of the shell is made of an elastic and/or plastic deformable material,
wherein the cavity comprises an interior step element, and wherein the insert comprises a corresponding step element configured to abut the interior step element and distribute at least a portion of the force from the plunger rod to the interior step element,
wherein the insert is constructed of a plurality of segments, whereby the segments decrease in size toward the distal end of the insert; and
wherein the shell is configured to be inserted into the housing prior to the container closure system being filled with a medical product, and the insert is configured to be inserted into the stopper after the container closure system has been filled with the medical product.

14. The container closure system of claim 13, wherein the container closure system is a syringe, and the housing is a housing of the syringe, and wherein the insert is disposed at a distal end of a plunger rod of the syringe and is configured to be inserted into the shell of the stopper after the syringe is assembled into a medical device.

15. The container closure system of claim 13, wherein the cartridge or the syringe is configured for use with one or more of: an autoinjector, a pen injector, or an injection pump.

16. The container closure system of claim 13, wherein the cartridge or the syringe contains a liquid medicament.

17. The container closure system of claim 13, wherein the cavity defines inwardly tapering sidewalls from the open end to the closed end of the shell, and wherein the inwardly tapering sidewalls are configured to maintain an inward taper when an arch region defining the convex surface in the cavity is deflected by the insert.

18. The container closure system of claim 13, wherein the insert comprises an electronic device having a sensor configured to generate a sensing signal, wherein the closed end of the shell is configured to allow the sensing signal to pass therethrough.

19. A stopper configured to be disposed within a container closure system, the stopper comprising:
a shell having a closed end and an open end with sidewalls extending between the closed end and the open end along a longitudinal axis of the shell, and
an insert configured to be inserted into a cavity of the stopper, the insert comprising a distal end and a proximal end and being sized and shaped to receive a force from a plunger rod and distribute the force to the shell in order to advance the shell into the container closure system, wherein the open end of the shell defines the cavity and the sidewalls define an exterior surface sized and shaped to fit inside the container closure system, wherein the closed end of the shell defines an arch region defining a convex surface that is curved into the cavity and a concave exterior surface of the closed end of the shell, wherein the cavity comprises an interior step element, and wherein the insert comprises a corresponding step element configured to abut the interior step element and distribute at least a portion of the force from the plunger rod to the interior step element, wherein the insert is constructed of a plurality of segments, whereby the segments decrease in size toward the distal end of the insert, and wherein the arch region is configured to be deflected by the insert contacting the convex surface upon insertion into the cavity.

* * * * *

UNITED STATES PATENT AND TRADEMARK OFFICE
CERTIFICATE OF CORRECTION

PATENT NO. : 12,337,151 B2  
APPLICATION NO. : 16/968735  
DATED : June 24, 2025  
INVENTOR(S) : Bernd Kuehn Page 1 of 1

It is certified that error appears in the above-identified patent and that said Letters Patent is hereby corrected as shown below:

On the Title Page

Column 2, Line 2 under Item (57) "ABSTRACT", delete "$_{[SL6]}$is" and insert -- is --

Signed and Sealed this  
Nineteenth Day of August, 2025

Coke Morgan Stewart  
*Acting Director of the United States Patent and Trademark Office*